(12) United States Patent
Ciavarella et al.

(10) Patent No.: US 10,143,339 B2
(45) Date of Patent: *Dec. 4, 2018

(54) SEQUENTIALLY ACTIVATED MULTI-DIAPHRAGM FOAM PUMPS, REFILL UNITS AND DISPENSER SYSTEMS

(71) Applicant: GOJO Industries, Inc., Akron, OH (US)

(72) Inventors: Nick E. Ciavarella, Seven Hills, OH (US); Dennis K. Jenkins, Akron, OH (US); Aaron D. Marshall, Uniontown, OH (US)

(73) Assignee: GOJO Industries, Inc., Akron, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/480,711

(22) Filed: Apr. 6, 2017

(65) Prior Publication Data

US 2017/0290470 A1    Oct. 12, 2017

Related U.S. Application Data

(63) Continuation-in-part of application No. 15/429,389, filed on Feb. 10, 2017, and a continuation-in-part of
(Continued)

(51) Int. Cl.
*A47K 5/16* (2006.01)
*A47K 5/14* (2006.01)
(Continued)

(52) U.S. Cl.
CPC ............. *A47K 5/14* (2013.01); *A47K 5/16* (2013.01); *A61K 31/045* (2013.01);
(Continued)

(58) Field of Classification Search
CPC .... F04B 13/02; F04B 43/0045; F04B 43/025; F04B 43/026; F04B 43/04; F04B 53/10;
(Continued)

(56) References Cited

U.S. PATENT DOCUMENTS 3,937,364 A    2/1976   Wright
3,970,219 A    7/1976   Sptizer
(Continued)

FOREIGN PATENT DOCUMENTS

CN    202370781 U    8/2012
CN    202493407 U    10/2012
(Continued)

OTHER PUBLICATIONS

Office Action for U.S. Appl. No. 15/355,112 dated Dec. 29, 2017.
(Continued)

*Primary Examiner* — Patrick M Buechner
(74) *Attorney, Agent, or Firm* — Calfee, Halter & Griswold LLP

(57) ABSTRACT

An exemplary foam dispenser includes a housing, a drive motor and a foam pump operatively coupled to the drive motor. The foam pump is secured to the housing and the foam pump includes a housing and a molded multi-chamber diaphragm. The molded multi-chamber diaphragm includes a liquid pump chamber, two or more air pump chambers; and an outlet valve. A mixing chamber is included and located downstream of the outlet valve for mixing foamable liquid from the liquid pump diaphragm with air from each of the two or more air pump chambers. In addition, a foam cartridge and an outlet for dispensing foam are also included.

20 Claims, 22 Drawing Sheets

Related U.S. Application Data application No. 15/369,007, filed on Dec. 5, 2016, and a continuation-in-part of application No. 15/356,795, filed on Nov. 21, 2016, and a continuation-in-part of application No. 15/355,112, filed on Nov. 18, 2016, and a continuation-in-part of application No. 15/350,190, filed on Nov. 14, 2016.

(60) Provisional application No. 62/319,061, filed on Apr. 6, 2016.

(51) Int. Cl.

| | | |
|---|---|---|
| B05B 7/00 | (2006.01) | |
| B05B 7/04 | (2006.01) | |
| F04B 43/02 | (2006.01) | |
| F04B 45/04 | (2006.01) | |
| F04B 53/10 | (2006.01) | |
| A61K 31/045 | (2006.01) | |
| B05B 7/24 | (2006.01) | |
| F04B 13/02 | (2006.01) | |
| F04B 19/06 | (2006.01) | |
| F04B 23/02 | (2006.01) | |
| F04B 23/06 | (2006.01) | |
| F04B 43/04 | (2006.01) | |
| F04B 45/047 | (2006.01) | |
| F04B 49/06 | (2006.01) | |

(52) U.S. Cl.
CPC .......... *B05B 7/0018* (2013.01); *B05B 7/0062* (2013.01); *B05B 7/0416* (2013.01); *B05B 7/2402* (2013.01); *F04B 13/02* (2013.01); *F04B 19/06* (2013.01); *F04B 23/02* (2013.01); *F04B 23/06* (2013.01); *F04B 43/02* (2013.01); *F04B 43/025* (2013.01); *F04B 43/026* (2013.01); *F04B 43/04* (2013.01); *F04B 45/04* (2013.01); *F04B 45/043* (2013.01); *F04B 45/047* (2013.01); *F04B 49/06* (2013.01); *F04B 53/10* (2013.01)

(58) Field of Classification Search
CPC ........ F04B 43/02; F04B 45/04; F04B 7/0038; F04B 7/0233; F04B 7/0275; A47K 5/12; A47K 5/14; A47K 5/16; B05B 11/3087; B05B 7/0018; B05B 7/0416
See application file for complete search history.

(56) References Cited

U.S. PATENT DOCUMENTS

| | | | |
|---|---|---|---|
| 4,022,351 A | 5/1977 | Wright | |
| 4,044,923 A | 8/1977 | Gardner | |
| 4,049,830 A | 9/1977 | Pugliese | |
| 4,184,615 A | 1/1980 | Wright | |
| 4,219,159 A | 8/1980 | Wesner | |
| 4,274,594 A | 6/1981 | Ito | |
| 4,371,517 A | 2/1983 | Vanlerberghe | |
| 4,678,668 A | 7/1987 | Darras | |
| 4,801,249 A | 1/1989 | Kakizawa | |
| 4,940,702 A | 7/1990 | Finch | |
| 4,945,110 A | 7/1990 | Brokken | |
| 5,028,407 A | 7/1991 | Finch | |
| 5,063,249 A | 11/1991 | Andrews | |
| 5,129,550 A | 7/1992 | Eschbach | |
| 5,208,257 A | 5/1993 | Kabara | |
| 5,370,815 A | 12/1994 | Kessler | |
| 5,529,770 A | 6/1996 | McKinzie | |
| 5,534,266 A | 7/1996 | Ricketts | |
| 5,575,993 A | 11/1996 | Ward | |
| 5,616,348 A | 4/1997 | Winicov | |
| 5,635,469 A | 6/1997 | Fowler | |
| 5,720,984 A | 2/1998 | Ricketts | |
| 5,791,882 A | 8/1998 | Stucker et al. | |
| 5,842,607 A | 12/1998 | Snider | |
| 5,843,912 A | 12/1998 | Hosmane | |
| 5,967,202 A | 10/1999 | Mullen | |
| 6,082,586 A | 7/2000 | Banks | |
| 6,264,438 B1 | 7/2001 | Fukami | |
| 6,302,058 B1 | 10/2001 | Dahl | |
| 6,382,928 B1 | 5/2002 | Chang | |
| 6,544,539 B1 | 4/2003 | Ricketts | |
| 6,871,679 B2 | 3/2005 | Last | |
| 7,040,876 B2 | 5/2006 | Fukami et al. | |
| 7,451,687 B2 | 11/2008 | Lynn | |
| 7,647,954 B2 | 1/2010 | Garber et al. | |
| 7,850,049 B2 | 12/2010 | Ciavarella et al. | |
| 7,887,304 B2 | 2/2011 | Cal | |
| 8,272,539 B2 | 9/2012 | Ophardt et al. | |
| 8,276,784 B2 | 10/2012 | Ciavarella | |
| 8,304,375 B1 | 11/2012 | Wolff | |
| 8,449,267 B2 | 5/2013 | Pascual | |
| 8,544,698 B2 | 10/2013 | Ciavarella et al. | |
| 8,734,132 B2 | 5/2014 | Brender a Brandis | |
| 8,763,863 B2 | 7/2014 | Quinlan et al. | |
| 8,820,585 B1 | 9/2014 | Banks | |
| 8,845,309 B2 | 9/2014 | Cal | |
| 8,955,718 B2 | 2/2015 | Ciavarella et al. | |
| 8,960,498 B2 | 2/2015 | Weglin et al. | |
| 9,341,176 B2 | 5/2016 | Itahara | |
| 9,596,963 B2 | 3/2017 | Harris et al. | |
| 2002/0051717 A1 | 5/2002 | Fukami | |
| 2003/0031571 A1 | 2/2003 | Yamakawa | |
| 2003/0068234 A1 | 4/2003 | Shindo | |
| 2003/0068242 A1 | 4/2003 | Yamakawa | |
| 2004/0266649 A1 | 12/2004 | Thekkekandam | |
| 2005/0049513 A1 | 3/2005 | Hori | |
| 2005/0258192 A1 | 11/2005 | Matthews | |
| 2006/0281663 A1 | 12/2006 | Asmus | |
| 2007/0148101 A1 | 6/2007 | Snyder | |
| 2007/0237901 A1 | 10/2007 | Moses | |
| 2008/0051314 A1 | 2/2008 | Wenzel | |
| 2009/0200340 A1 | 8/2009 | Ophardt | |
| 2009/0294478 A1 | 12/2009 | Ciavarella | |
| 2009/0317270 A1 | 12/2009 | Reynolds | |
| 2010/0051642 A1 | 3/2010 | Wong | |
| 2010/0102083 A1 | 4/2010 | Quinlan | |
| 2010/0270328 A1 | 10/2010 | Quinlan | |
| 2012/0285992 A1 | 11/2012 | Ciavarella et al. | |
| 2012/0309660 A1 | 12/2012 | Kawasoe | |
| 2012/0315166 A1 | 12/2012 | Looi et al. | |
| 2013/0017110 A1 | 1/2013 | Villagomez | |
| 2013/0032614 A1* | 2/2013 | Babikian | B01F 5/0693 222/190 |
| 2013/0056497 A1 | 3/2013 | McNulty | |
| 2013/0165530 A1 | 6/2013 | Hillman | |
| 2013/0175296 A1 | 7/2013 | Gray | |
| 2013/0200098 A1 | 8/2013 | Li | |
| 2013/0206794 A1 | 8/2013 | McNulty et al. | |
| 2013/0233441 A1 | 9/2013 | Ciavarella | |
| 2014/0054322 A1 | 2/2014 | McNulty et al. | |
| 2014/0054323 A1 | 2/2014 | McNulty et al. | |
| 2014/0061246 A1 | 3/2014 | McNulty | |
| 2014/0117053 A1 | 5/2014 | Ciavarella | |
| 2014/0154117 A1 | 6/2014 | Fukami | |
| 2014/0189992 A1 | 7/2014 | Ganzeboom | |
| 2014/0202047 A1 | 7/2014 | McNulty | |
| 2014/0203047 A1 | 7/2014 | McNulty | |
| 2014/0234140 A1 | 8/2014 | Curtis et al. | |
| 2014/0243417 A1 | 8/2014 | Modak | |
| 2014/0367419 A1 | 12/2014 | Harris et al. | |
| 2015/0025156 A1 | 1/2015 | Hillman | |
| 2015/0080478 A1 | 3/2015 | Cohen | |
| 2015/0090737 A1 | 4/2015 | Ciavarella | |
| 2015/0209811 A1 | 7/2015 | Ophardt et al. | |
| 2015/0251841 A1 | 9/2015 | McNulty et al. | |
| 2015/0266657 A1 | 9/2015 | Corney | |
| 2015/0297728 A1 | 10/2015 | Charboneau | |
| 2015/0320266 A1 | 11/2015 | Creaghan | |
| 2015/0337820 A1 | 11/2015 | Cai | |
| 2016/0029855 A1 | 2/2016 | Harris et al. | |
| 2016/0256016 A1 | 9/2016 | Yang | |

(56) References Cited

U.S. PATENT DOCUMENTS

| | | |
|---|---|---|
| 2017/0135531 A1 | 5/2017 | Mak |
| 2017/0135532 A1 | 5/2017 | Ciavarella |
| 2017/0136475 A1 | 5/2017 | Twaroski |
| 2017/0143172 A1 | 5/2017 | Ciavarella |
| 2017/0156550 A1 | 6/2017 | Ciavarella |
| 2017/0231437 A1 | 8/2017 | Ciavarella |

FOREIGN PATENT DOCUMENTS

| | | |
|---|---|---|
| CN | 103742391 A | 4/2014 |
| CN | 203570550 U | 4/2014 |
| CN | 203867833 U | 10/2014 |
| CN | 204003387 U | 12/2014 |
| EP | 2135538 A1 | 12/2009 |
| EP | 3064114 A1 | 9/2016 |
| JP | 2004301300 A | 10/2004 |
| WO | 2012154642 A1 | 11/2012 |
| WO | 2013126696 A2 | 8/2013 |

OTHER PUBLICATIONS

Office Action for U.S. Appl. No. 15/369,007 dated Dec. 29, 2017.
Office Action for U.S. Appl. No. 15/356,795 dated Jan. 12, 2018.
Notice of Allowance for U.S. Appl. No. 15/530,185 dated Dec. 13, 2017.
Office Action for U.S. Appl. No. 15/350,190 dated Dec. 18, 2017.
Notice of Allowance for U.S. Appl. No. 15/355,112 dated May 21, 2018.
Notice of Allowance for U.S. Appl. No. 15/369,007 dated May 22, 2018.
Notice of Allowance for U.S. Appl. No. 15/350,190 dated May 8, 2018.
Office Action for U.S. Appl. No. 15/429,389 dated Feb. 23, 2018.
Notice of Allowance for U.S. Appl. No. 15/356,795 dated May 21, 2018.

\* cited by examiner

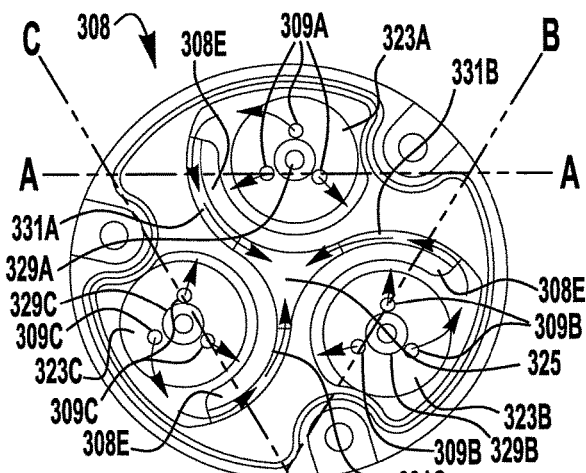
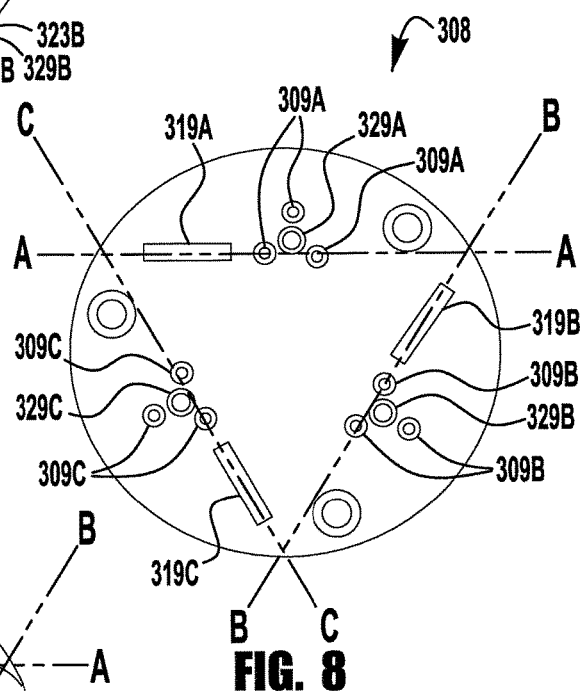
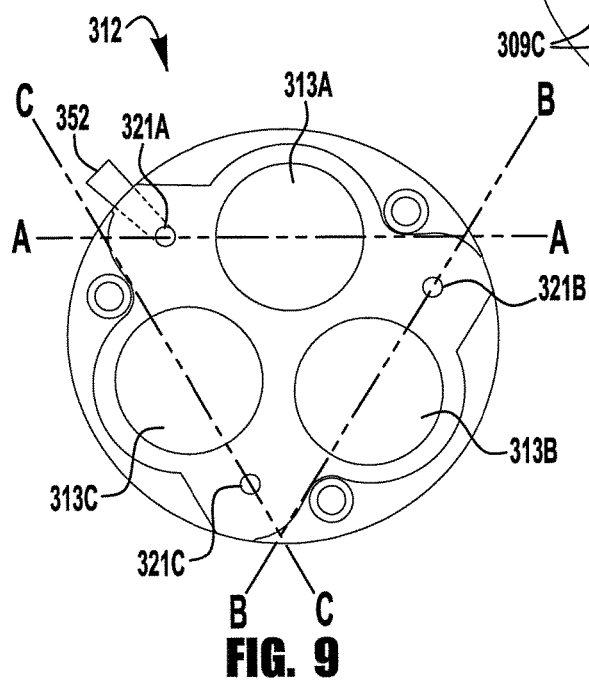
FIG. 7
FIG. 8
FIG. 9

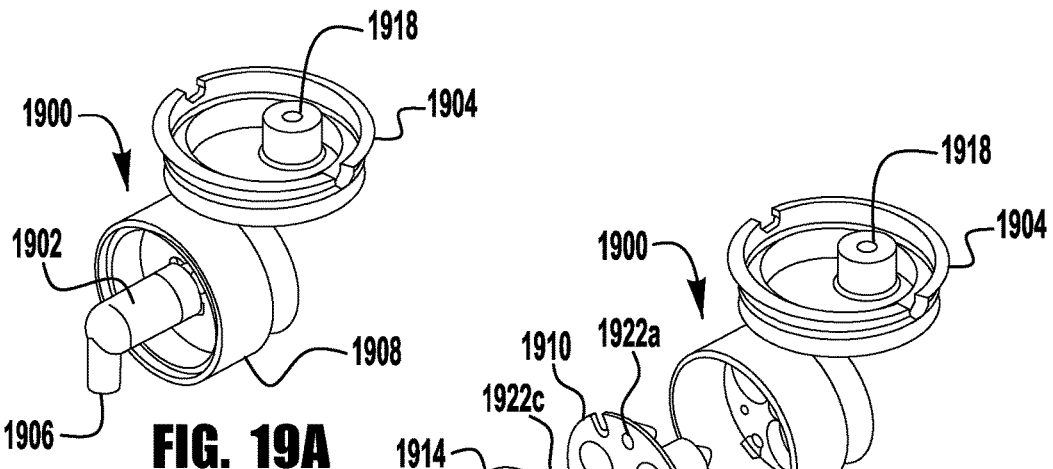
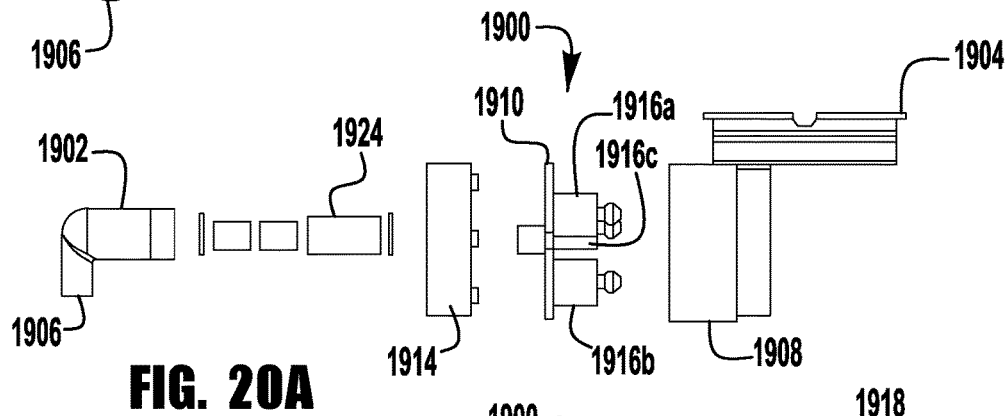
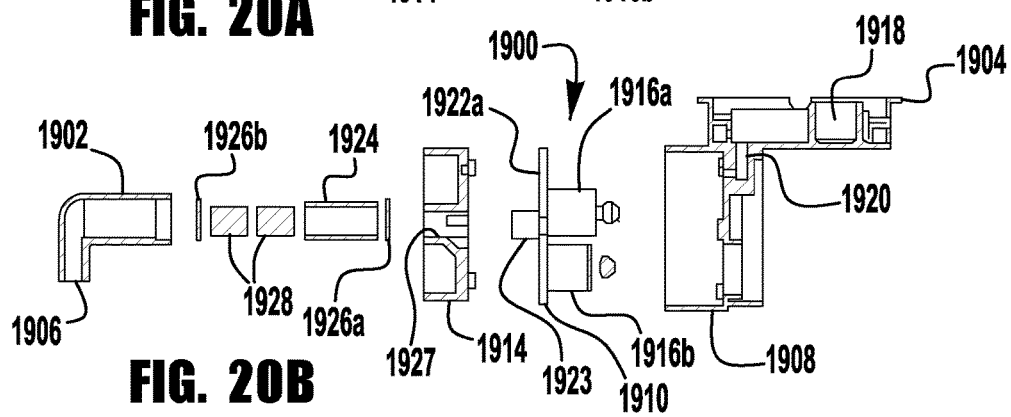

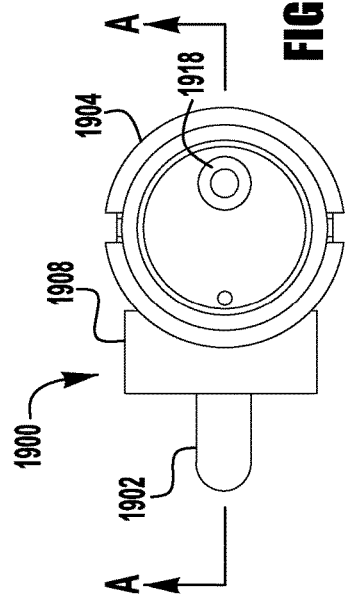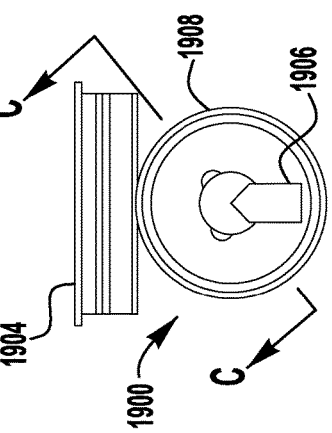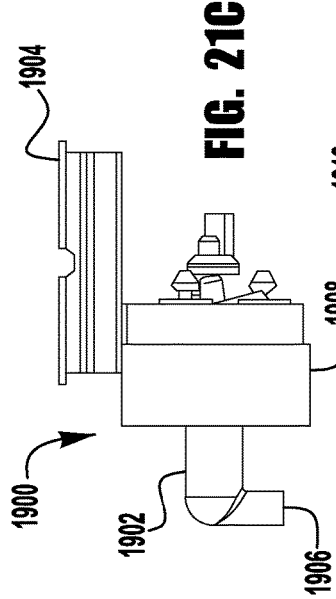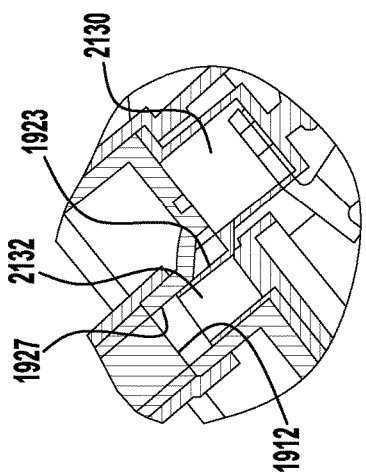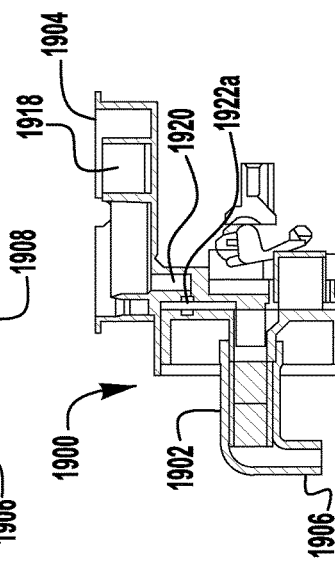
FIG. 21A
FIG. 21B
FIG. 21C
FIG. 21D
FIG. 21E

SEQUENTIALLY ACTIVATED MULTI-DIAPHRAGM FOAM PUMPS, REFILL UNITS AND DISPENSER SYSTEMS

RELATED APPLICATIONS

The present invention claims priority to, and the benefits of: U.S. Provisional Application Ser. No. 62/319,061 filed on Apr. 6, 2016 and titled SEQUENTIALLY ACTIVATED MULTI-DIAPHRAGM FOAM PUMPS, REFILL UNITS AND DISPENSER SYSTEMS; U.S. Non-Provisional application Ser. No. 15/429,389 filed on Feb. 10, 2017 and titled HIGH QUALITY NON-AEROSOL HAND SANITIZING FOAM; U.S. Non-Provisional application Ser. No. 15/369,007 filed on Dec. 5, 2016 and titled SEQUENTIALLY ACTIVATED MULTI-DIAPHRAGM FOAM PUMPS, REFILL UNITS AND DISPENSER SYSTEMS; U.S. Non-Provisional patent application Ser. No. 15/355,112 filed on Nov. 18, 2016 and titled SEQUENTIALLY ACTIVATED MULTI-DIAPHRAGM FOAM PUMPS, REFILL UNITS AND DISPENSER SYSTEMS; U.S. Non-Provisional application Ser. No. 15/350,190 filed on Nov. 14, 2016 and titled IMPROVED FOAMING CARTRIDGE; and U.S. Non-Provisional application Ser. No. 15/356,795 filed on Nov. 21, 2016 and titled FOAM DISPENSING SYSTEMS, PUMPS AND REFILL UNITS HAVING HIGH AIR TO LIQUID RATIOS. Each of which are incorporated herein by reference in their entirety.

TECHNICAL FIELD

The present invention relates generally to pumps, refill units for dispenser systems, and more particularly to pumps, refill units, and dispensers having sequentially activated multi-diaphragm foam pumps for mixing liquid soap, sanitizer, or lotion with air to create and dispense a foam product.

BACKGROUND OF THE INVENTION

Liquid dispenser systems, such as liquid soap and sanitizer dispensers, provide a user with a predetermined amount of liquid upon actuation of the dispenser. In addition, it is sometimes desirable to dispense the liquid in the form of foam by, for example, injecting air into the liquid to create a foamy mixture of liquid and air bubbles.

SUMMARY

The present application discloses exemplary embodiments of sequentially activated multi-diaphragm foam pumps, refill units and dispenser systems and refill units sequentially activated multi-diaphragm foam pumps.

An exemplary foam dispenser includes a housing, a drive motor and a foam pump operatively coupled to the drive motor. The foam pump is secured to the housing and the foam pump includes a housing and a molded multi-chamber diaphragm. The molded multi-chamber diaphragm includes a liquid pump chamber, two or more air pump chambers; and an outlet valve. A mixing chamber is included and located downstream of the outlet valve for mixing foamable liquid from the liquid pump diaphragm with air from each of the two or more air pump chambers. In addition, a foam cartridge and an outlet for dispensing foam are also included.

An exemplary refill unit for a foam dispenser includes a container for holding foamable liquid, a foam pump secured to the container. The foam pump includes a housing, a molded multi-chamber diaphragm. The molded multi-chamber diaphragm includes a liquid pump chamber and three air pump chambers. The foam pump also includes an inlet valve, an outlet valve, and a mixing chamber downstream of the outlet valve for mixing foamable liquid from the liquid pump chamber with air from each of the three air pump chambers. The refill unit further includes a foam cartridge in fluid communication with the mixing chamber and an outlet for dispensing foam wherein the outlet is in fluid communication with the foam cartridge.

Another exemplary foam dispenser includes a dispenser housing and a foam pump secured to the housing. The foam pump includes a pump housing and a molded multi-chamber diaphragm. The molded multi-chamber diaphragm includes a liquid pump chamber and three air pump chambers. A rotatable drive mechanism for sequentially compressing the liquid pump chamber and two or more air pump chambers is also included. The rotatable drive mechanism is coupled to a drive motor. A mixing chamber is located downstream of the liquid and air pump chambers for mixing foamable liquid from the liquid pump chamber with air from each of the three air pump chambers. A foam cartridge is included and is in fluid communication with the mixing chamber. In addition, the dispenser includes an outlet for dispensing foam wherein the outlet is in fluid communication with the foam cartridge.

An exemplary refill unit for a foam dispenser includes a container for holding foamable liquid, a foam pump secured to the container, a foam cartridge, an outlet and an actuation mechanism. The foam pump includes a housing, a liquid pump diaphragm, a plurality of air pump diaphragms, and a mixing chamber. Liquid from the liquid pump diaphragm and air from the air pump diaphragms mix in the mixing chamber to form a foamy mixture. The foam cartridge is in fluid communication with the mixing chamber, and the foamy mixture travels through the foam cartridge. A dose of foam exits the foam cartridge, and the dose of foam is dispensed out of the outlet of the refill unit. An actuation mechanism releasably connects to a drive system that is permanently attached to a dispenser. The actuation mechanism sequentially activates the liquid pump diaphragm and the air pump diaphragms when the refill unit is connected to the dispenser and the drive system is activated. The sequential activation of the liquid pump diaphragm and air pump diaphragms causes the liquid pump diaphragm to pump at least a partial dose of liquid into the mixing chamber and the air pump diaphragms to pump at least a partial dose of air into the mixing chamber.

Another exemplary refill unit for a foam dispenser includes a container for holding foamable liquid, a foam pump connected to the container, a mixing chamber, a foam cartridge, an outlet, and a plate. The foam pump has a plurality of diaphragm pumping chambers. At least one diaphragm pumping chamber pumps liquid, and at least two diaphragm pumping chambers pump air. The mixing chamber is located downstream of the plurality of diaphragm pumping chambers for mixing liquid and air to form a foamy mixture. The foam cartridge is located downstream of the mixing chamber, and the foamy mixture travels through the foam cartridge and exits the foam cartridge as an enriched foam. The foam is dispensed through the outlet of the refill unit. The plate is connected to the plurality of diaphragm pumping chambers. The plate is configured to engage with a drive system that is permanently secured to the foam dispenser when the refill unit is installed in the foam dispenser and disengage with the drive system when the refill unit is removed from the foam dispenser. Movement of the plate about an axis causes at least a partial dose of liquid to be pumped into the mixing chamber, followed by at least a partial dose of a first dose of air being pumped into the mixing chamber, followed by at least a partial dose of a second dose of air being pumped into the mixing chamber.

Another exemplary refill unit for a foam dispenser includes a container for holding foamable liquid, a sequentially activated multi-diaphragm foam pump secured to the container, a wobble plate, a pin, a foam cartridge, and a foam outlet. The sequentially activated multi-diaphragm foam pump has a liquid pump diaphragm for pumping liquid into a mixing chamber, a first air pump diaphragm for pumping air into the mixing chamber, and a second air pump diaphragm for pumping air into the mixing chamber. The wobble plate is secured to the liquid pump diaphragm, the first air pump diaphragm, and the second air pump diaphragm. The pin has a first end that is connected to the wobble plate and a second end that is free. Movement of the second end of the pin in a circular path causes a sequential compression of the liquid pump diaphragm, the first air pump diaphragm, and the second air pump diaphragm. The second end of the pin is releasably connected to an eccentric drive system that is permanently connected to the foam dispenser. The foam cartridge is downstream from the mixing chamber, and the foam outlet is downstream of the foam cartridge. Foam is dispensed from the foam outlet.

Another exemplary refill unit for a foam dispenser includes a container for holding foamable liquid, a sequentially activated multi-diaphragm foam pump, a plate, a foam cartridge, and an outlet. The sequentially activated multi-diaphragm foam pump includes a housing, a liquid pump portion secured to the housing, an air pump portion secured to the housing, a mixing chamber, and a pump outlet. The liquid pump portion has a liquid inlet, a liquid inlet valve, a liquid pump diaphragm, a liquid outlet valve, and a liquid outlet. The air pump portion has a first and second air inlet, a first and second air inlet valve, a first and second air pump diaphragm, a first and second air outlet valve, and a first and second air outlet. The mixing chamber is in fluid communication with the liquid outlet, the first air outlet, and the second air outlet. The liquid pump diaphragm pumps a shot of liquid into the mixing chamber. The first air pump diaphragm pumps a shot of air into the mixing chamber to mix with the liquid to form a liquid air mixture. The second air pump diaphragm pumps a shot of air into the mixing chamber to mix with the liquid air mixture to form a foamy mixture. The foamy mixture is dispensed from the pump outlet. The plate is connected to the liquid pump diaphragm, the first air pump diaphragm, and the second air pump diaphragm. The plate is configured to engage with a drive system that is permanently secured to the foam dispenser when the refill unit is installed in the foam dispenser and disengage with the drive system when the refill unit is removed from the foam dispenser. Movement of the plate about an axis causes the shot of liquid to be pumped from the liquid pump diaphragm into the mixing chamber, followed by the shot of air to be pumped from the first air pump diaphragm into the mixing chamber, followed by the shot of air to be pumped from the second air pump diaphragm into the mixing chamber. The foam cartridge is in fluid communication with the pump outlet, and the outlet of the refill unit is in fluid communication with the foam cartridge. Foam is dispensed from the outlet of the refill unit. In addition, some exemplary refill units do not contain a plate and the drive mechanism on the foam dispenser is configured to sequentially compress the diaphragms without the need for the plate.

BRIEF DESCRIPTION OF THE DRAWINGS

FIG. 7 is a top view of an exemplary valve seat for the exemplary embodiment of the sequentially activated multi-diaphragm foam pump of FIG. 3;

FIG. 8 is a bottom view of the exemplary valve seat of FIG. 7;

FIG. 9 is a top view of an exemplary diaphragm assembly seat for the exemplary embodiment of the sequentially activated multi-diaphragm foam pump of FIG. 3;

FIG. 19A is a perspective view of another exemplary embodiment of a sequentially-activated multi-diaphragm foam pump;

FIG. 19B is an exploded perspective view of the sequentially-activated multi-diaphragm foam pump of FIG. 19A;

FIG. 20A is an exploded side view of the exemplary embodiment of the sequentially-activated multi-diaphragm foam pump of FIG. 19A;

FIG. 20B is a cross-sectional exploded side view of the exemplary embodiment of the sequentially-activated multi-diaphragm foam pump of FIG. 19A;

FIG. 21A is a top view of the exemplary embodiment of the sequentially-activated multi-diaphragm foam pump of FIG. 19A;

FIG. 21B is a front view of the exemplary embodiment of the sequentially-activated multi-diaphragm foam pump of FIG. 19A;

FIG. 21C is a side view of the exemplary embodiment of the sequentially-activated multi-diaphragm foam pump of FIG. 19A;

FIG. 21D is a cross-sectional side view taken along the lines A-A of FIG. 21A of the exemplary embodiment of the sequentially-activated multi-diaphragm foam pump of FIG. 19A;

FIG. 21E is a cross-sectional view taken along the lines C-C of FIG. 21B of the exemplary embodiment of the sequentially-activated multi-diaphragm foam pump of FIG. 19A;

DETAILED DESCRIPTION

The present application discloses exemplary embodiments of foam dispensers, and refill units that having sequentially activated multi-diaphragm foam pumps. Some exemplary embodiments include a wobble plate and three or more pump diaphragms. The three or more pump diaphragms include at least one liquid pump diaphragm and at least two air pump diaphragms. Each liquid pump diaphragm has a liquid inlet for receiving liquid, such as, for example, a soap, a sanitizer, or a lotion, and each air pump diaphragm has an air inlet for receiving air. The three or more pump diaphragms operate sequentially, and each pump diaphragm operates once in an operating cycle. An operating cycle begins with the operation of a liquid pump diaphragm. Additionally, the sequentially activated multi-diaphragm foam pump includes a mixing chamber. Each liquid pump diaphragm pumps liquid into the mixing chamber, and each air pump diaphragm pumps air into the mixing chamber. The liquid mixes with the air in the mixing chamber to create a foam mixture that is dispensed out of the pump outlet. In some embodiments of the present invention, the foam mixture has an air to liquid ratio of between about 7 to 1 and about 10 to 1. In some embodiments, the air to liquid ratio is greater than 10 to 1, and in some embodiments is less than 7 to 1.

The sequentially activated multi-diaphragm foam pumps may be used in foam dispensers. An exemplary foam dispenser comprises a housing, a motor, a refill unit, a sequentially activated multi-diaphragm foam pump, and a foam cartridge. The pump receives a foamable liquid from the refill unit, mixes the foamable liquid with air to create a foam mixture, forces the foam mixture through the foam cartridge to enrich the foam, and dispenses the foam to a user.

Figure 1:
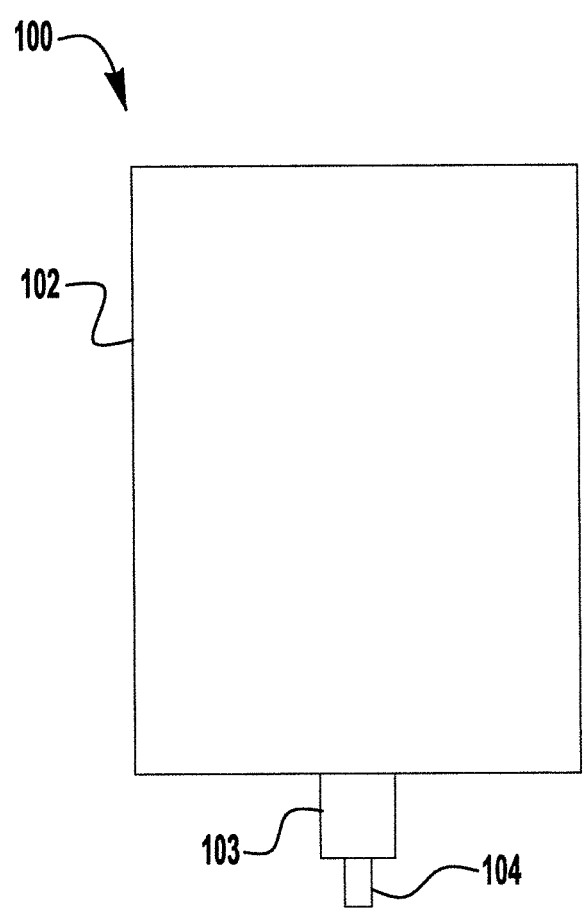
FIG. 1 is an exemplary embodiment of a refill unit for a foam dispenser.

FIG. 1 illustrates a refill unit 100 for a foam dispenser. The refill unit 100 includes a collapsible container 102. Collapsible container 102 includes a neck 103 and a drip-free quick connector 104. Exemplary drip-free quick connectors are disclosed in U.S. Pat. No. 6,871,679 titled Bag and Dispensing System Comprising Such A Bag, and U.S. Pat. No. 7,647,954 titled Connector Apparatus And Method For Connecting The Same For Controlling Fluid Dispensing, which are incorporated herein by reference in their entirety. Refill units contain a supply of a foamable liquid. In various embodiments, the contained foamable liquid could be for example a soap, a sanitizer, a cleanser, a disinfectant, a lotion or the like. The container is a collapsible container and can be made of thin plastic or a flexible bag-like material. In other embodiments, the container may be a non-collapsing container formed by a rigid housing member, or any other suitable configuration for containing the foamable liquid without leaking. In the case of a non-collapsing container, a vent system may be included. Exemplary venting systems are disclosed in U.S. Patent Applications Publication No. 2015/0266657 titled Closed system for venting a dispenser reservoir; Publication No. 2015/025184 titled Pumps With Container Vents and application Ser. No. 14/811,995, titled Vented Refill Units And Dispensers Having Vented Refill Units, which are incorporated herein by reference.

Figure 2:
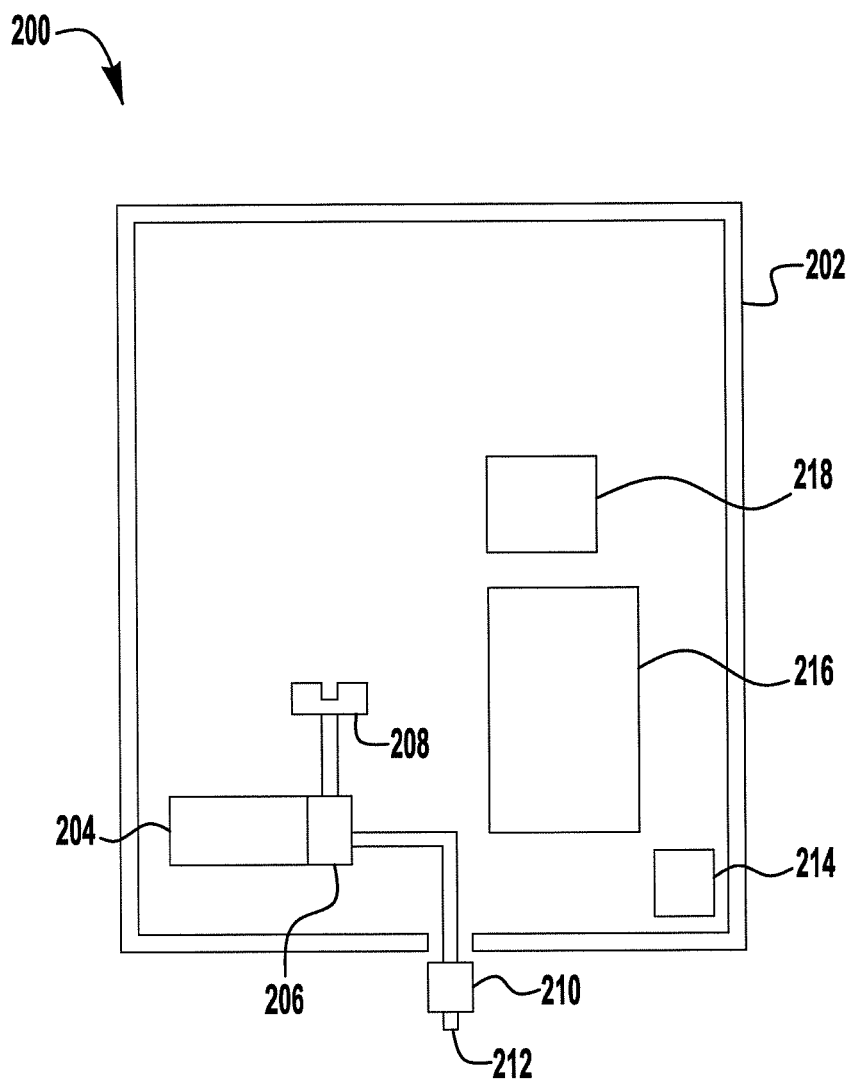
FIG. 2 is an exemplary embodiment of a foam dispenser.
Figure 2A:
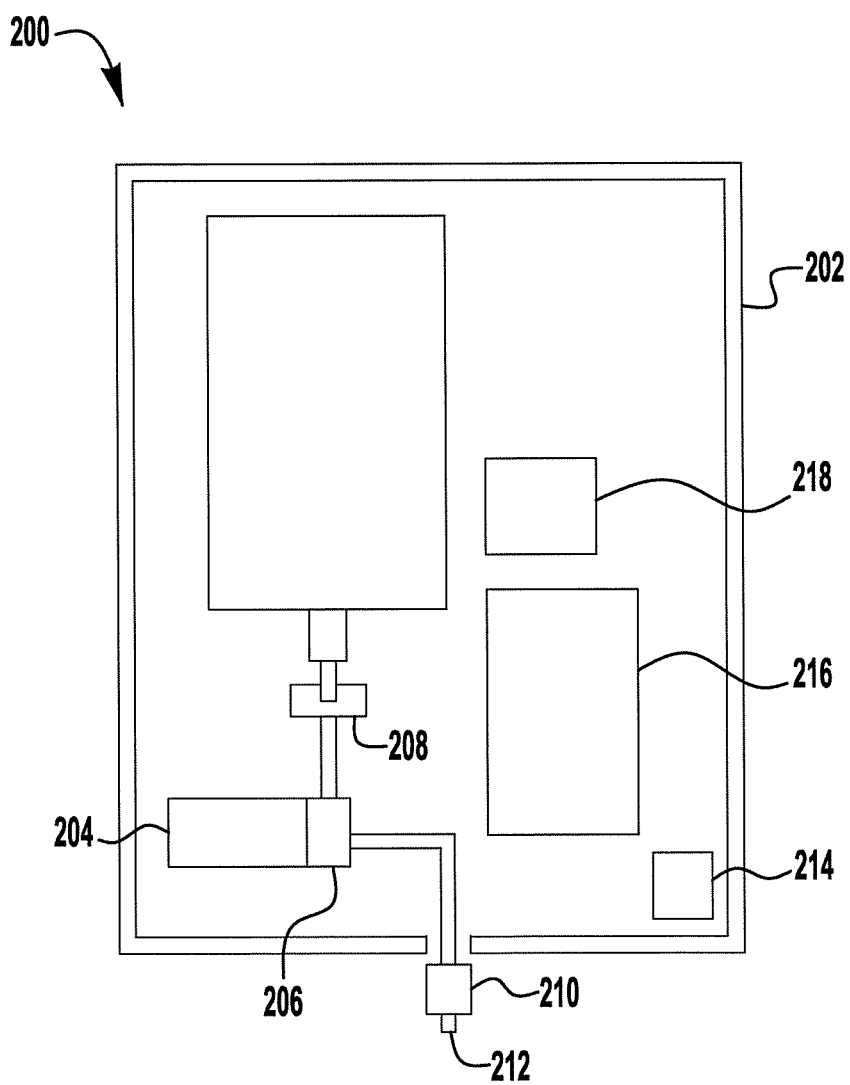
FIG. 2A is the exemplary foam dispenser of FIG. 2 with the exemplary refill unit of FIG. 1 installed.

FIG. 2 illustrates an exemplary embodiment of a touch-free foam dispenser 200. The touch-free foam dispenser 200 includes a housing 202, a motor 204, a foam pump 206, a refill unit connector 208, a foam cartridge 210, and a nozzle 212. Exemplary embodiments of foam cartridges 210 are shown and described in U.S. Publication No. 20140367419, which is incorporated herein in its entirety by reference. A refill unit 100 may be connected to the refill unit connector 208 as shown in FIG. 2A. The refill unit 100 contains a foamable liquid, such as a soap, a sanitizer, a lotion, a cleanser, a disinfectant or the like. The touch-free foam dispenser 200 is activated when sensor 214 detects the presence of a user or object. Upon detection of an object or user, the sensor 214 provides a signal to the processor (not shown) in the electronic control board 216. The electronic control board 216 provides an output signal that causes the motor 204 to rotate an eccentric wobble plate actuator drive mechanism 301. The sensor 214 and the electronic control board 216 receive power from a power source 218. In some embodiments, the motor 204 receives power from the power source 218, and, in other embodiments, the refill unit includes a power source (not shown) that provides power to a rechargeable power source (not shown). Exemplary embodiments of refill units with power supplies that provide power to the wobble plate actuator drive mechanism 301 (FIG. 3) are shown and described in U.S. Publication No. 2014/0234140 titled Power Systems For Touch Free Dispensers And Refill Units Containing A Power Source, which is incorporated herein in its entirety by reference. Providing power to the motor 204 causes wobble plate actuator drive mechanism 301 to rotate. Rotation of eccentric wobble plate actuator drive mechanism 301 sequentially compresses and expands the diaphragms of foam pump 206 and pumps liquid and air into mixing chamber 325. The liquid and air mix together and form a foamy mixture. The foamy mixture is forced through the foam cartridge 210, which enhances the foam into a rich foam. The rich foam is dispensed from the foam dispenser 200 through the nozzle 212.

The refill unit 100 and the foam dispenser 200 illustrated in FIGS. 1 and 2, respectively, are drawn generically because a variety of different components may be used for many of the refill unit 100 and the foam dispenser 200. Although foam pump 206 is illustrated generically above, it is described in detail below. Some exemplary dispenser components that may be used in accordance with the present invention are shown and described in U.S. Pat. No. 8,960,498 titled Touch-Free Dispenser With Single Cell Operation And Battery Banking; U.S. Pat. Pub. No. 2014/00543.22 titled Off-Axis Inverted Foam Dispensers And Refill Units and Pub. No. 2014/0234140 titled Power Systems For Touch Free Dispensers And Refill Units Containing a Power Source, which are incorporated herein by reference in their entirety.

Figure 3:
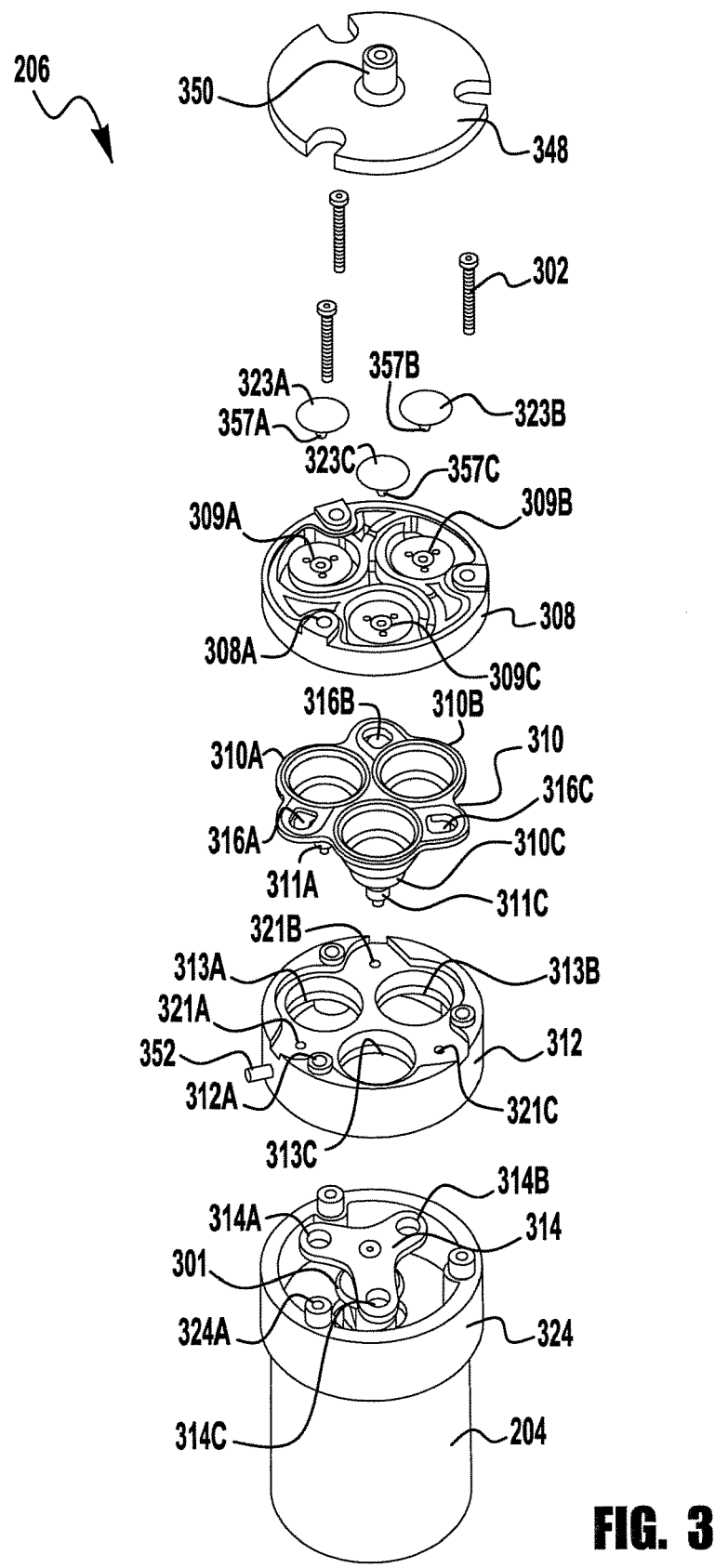
FIG. 3 is an exploded view of an exemplary embodiment of a sequentially activated multi-diaphragm foam pump and motor taken from a first perspective.

FIG. 3 is an exploded view of an exemplary embodiment of foam pump 206. Foam pump 206 is driven by motor 204. Foam pump 206 includes a pump base 324, a wobble plate 314, a diaphragm assembly seat 312, a diaphragm assembly 310, a valve seat 308, outlet valves 323A, 323B, 323C, screws 302, and a cover 348. The valve seat 308, diaphragm assembly seat 312, and pump base 324 are secured together by screws 302 in screw holes 308A, 312A, 324A. The cover 348 is attached to the valve seat 308. Outlet valves 323A, 323B 323C are secured to and seated in the valve seat 308.

The diaphragm assembly 310 includes three pump diaphragms 310A, 310B, 310C, and each pump diaphragm 310A, 310B, 310C has a connector 311A, 311B, 311C. The diaphragm assembly 310 is located in the diaphragm assembly seat 312. The pump diaphragms 310A, 310B, 310C are disposed in the receiving holes 313A, 313B, 313C of the diaphragm assembly seat 312, and the three connectors 311A, 311B, 311C connect to the wobble plate 314 by inserting the three connectors 311A, 311B, 311C in the three wobble plate links 314A, 314B, 314C.

Air enters the foam pump 206 through pump air inlet 424B (FIG. 4), and liquid, such as for example, foamable soap or sanitizer enters the foam pump 206 through liquid inlet 352. Two of the pump diaphragms 310B, 310C receive air, and the other pump diaphragm 310A receives foamable liquid, such as, for example soap or sanitizer.

Figure 4:
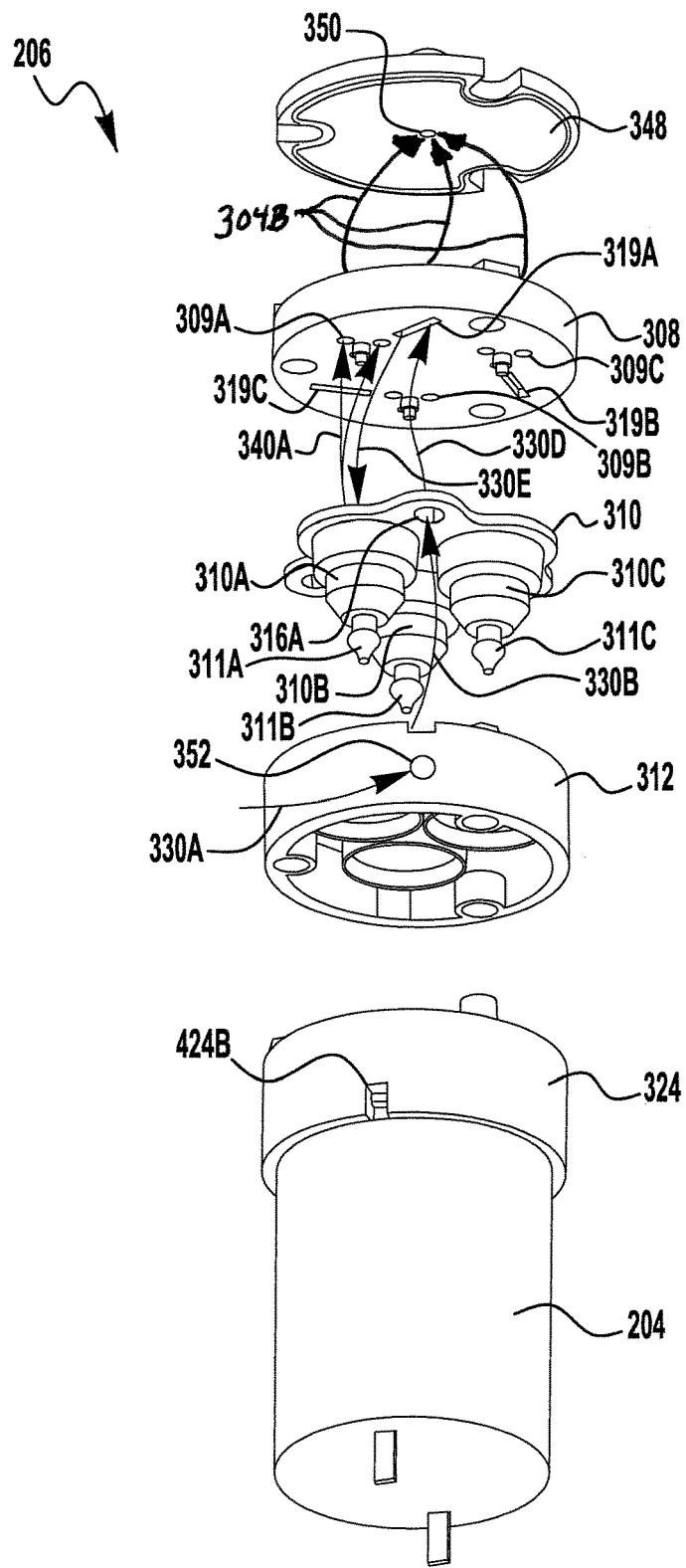
FIG. 4 is an exploded view of the exemplary embodiment of the sequentially activated multi-diaphragm foam pump and motor of FIG. 3 taken from a second perspective.

FIG. 4 is another exploded view of the exemplary foam pump 206 from a different perspective. As described above, the diaphragm assembly 310 includes three pump diaphragms 310A, 310B, 310C. Each pump diaphragm 310A, 310B, 310C has a corresponding inlet valve 316A, 316B, 316C (better seen in FIGS. 5 and 6). FIG. 4 also provides a view of the bottom of the valve seat 308. The bottom of valve seat 308 has three areas that correspond to the three pump diaphragms 310A, 310B, 310C. Each area has three fluid outlet apertures 309A, 309B, 309C that extend through valve seat 308, a valve stem retention aperture 329A, 329B, 329C (FIG. 7), and a fluid inlet groove 319A, 319B, 319C. The fluid inlet grooves 319A, 319B, 319C do not extend through valve seat 308.

Figure 5:
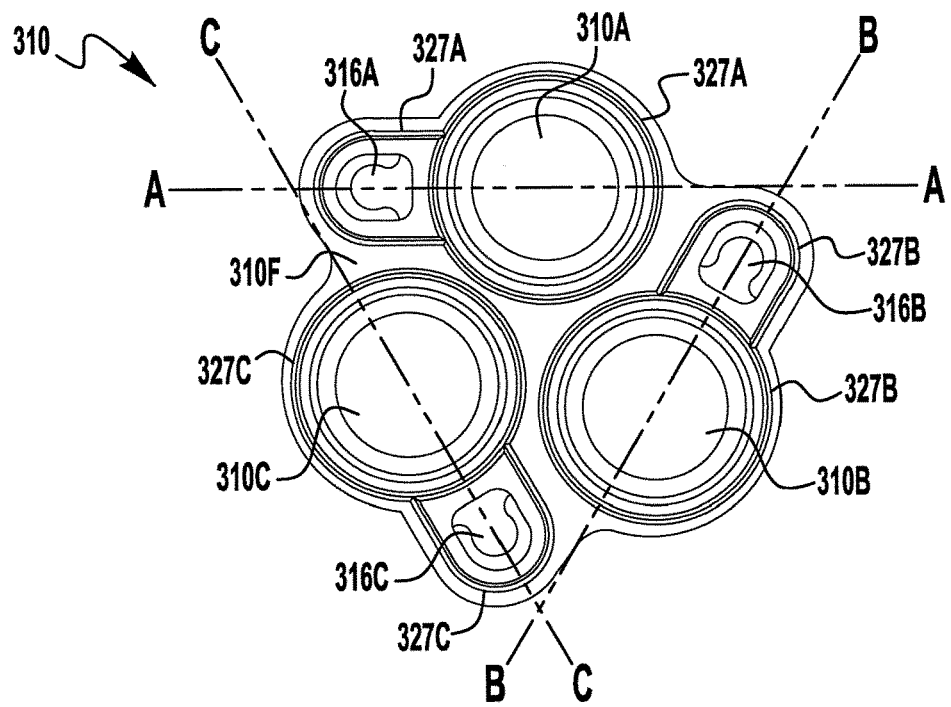
FIG. 5 is a top view of an exemplary diaphragm assembly for the exemplary embodiment of the sequentially activated multi-diaphragm foam pump of FIG. 3.
Figure 6:
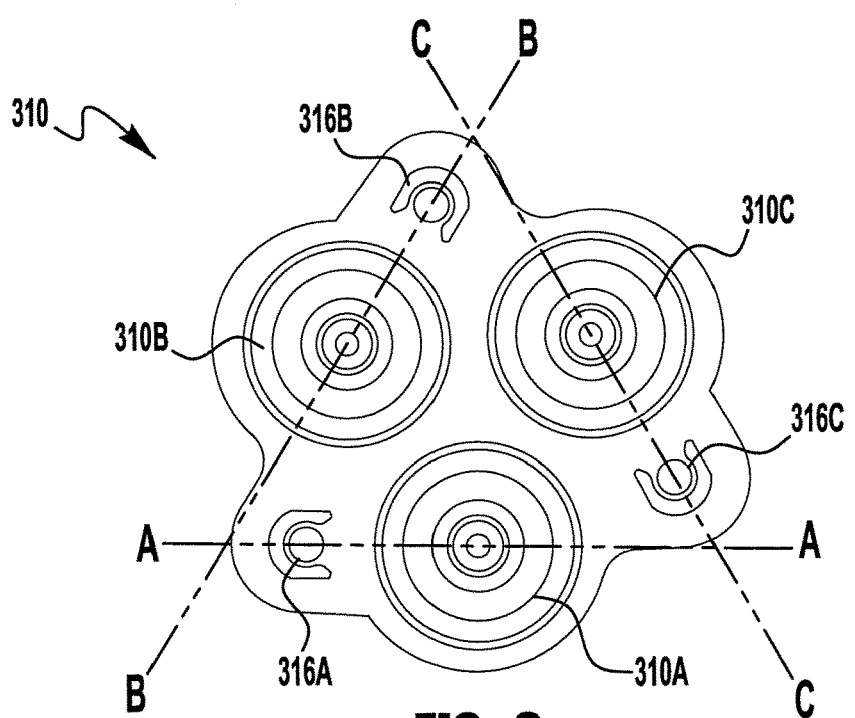
FIG. 6 is a bottom view of the exemplary diaphragm assembly of FIG. 5.

FIGS. 5 and 6 illustrate a top view and a bottom view, respectively, of the exemplary diaphragm assembly 310 for foam pump 206. In some embodiments, the diaphragm assembly is made of natural rubber, EPDM, Silicone, Silicone rubber TPE, TPU, TPV, vinyl, or the like. The diaphragm assembly 310 includes three molded pump diaphragms 310A, 310B, 310C and three corresponding inlet valves 316A, 316B, 316C. The top of the diaphragm assembly 310 acts as a sealing gasket. The top of the diaphragm assembly 310 has a flat section 310F, and each pump diaphragm 310A, 310B, 310C has gasket walls 327A, 327B, 327C that surround the respective valves 316A, 316B, 316C and pump diaphragms 310A, 310B, 310C. The gasket walls 327A, 327B, 327C seal against the bottom of the valve seat 308 (FIG. 4 and FIG. 8) to prevent fluid, such as, air and liquid soap or sanitizer from leaking out of the foam pump 206 at a location other than the pump outlet 350 (FIG. 3). One-way inlet valves 316A, 316B, 316C allow air, liquid soap, or sanitizer to enter the pump diaphragms 310A, 310B, 310C when the pump diaphragms 310A, 310B, 310C have a negative pressure (i.e., when the pump diaphragms 310A, 310B, 310C are expanding), and seal against inlet apertures 321A, 321B, 321C when the pump diaphragms 310A, 310B, 310C have a positive pressure (e.g. when the pump diaphragms 310A, 310B, 310C are compressing). The one-way inlet valves 316A, 316B, 316C are formed by flexible tabs and are made of the same material as the diaphragm assembly 310.

FIG. 7 is a top view of an exemplary valve seat 308 for the foam pump 206. One-way liquid outlet valve 323A is shown transparently to more clearly illustrate the flow of liquid 331A through liquid outlet apertures 309A and into mixing chamber 325. One-way liquid outlet valve 323A includes a valve stem 357A (FIG. 3) that is inserted into aperture 329A to secure one-way liquid outlet valve 323A to valve seat 308. One-way liquid outlet valve 323A is normally closed and prevents air or liquid from flowing from the mixing chamber 325, back through air outlet apertures 309A, and into liquid pump diaphragm 310A. One-way liquid outlet valve 323 opens when liquid pump diaphragm 310A is being compressed to pump fluid.

Similarly, one-way air outlet valves 323B, 323C are shown transparently to more clearly illustrate the flow of air 331B, 331C through air outlet apertures 309B, 309C and into mixing chamber 325. One-way air outlet valves 323B, 323C each include a valve stem 357B, 357C (FIG. 3) that are inserted into corresponding apertures 329B, 329C to secure the one-way air outlet valves to valve seat 308. One-way air outlet valves 323B, 323C are normally closed and prevent air or liquid from flowing from the mixing chamber 325, back through air outlet apertures 323B, 323C, and into air pump diaphragms 310B, 310C. One-way air outlet valves 323B, 323C open when corresponding air pump diaphragms 310B, 310C are being compressed to pump air.

The valve seat 308 also includes flow directional control walls 308E. The flow directional control walls 308E provide flow paths that aid in the mixing of liquid and air. In this embodiment the flow directional control walls 308E are curved and cause the liquid and air to intersect in a tangential relationship. In some embodiments, flow directional control walls 308E are designed and arranged to cause the liquid an air to intersect at a desired angle, such as, for example, each flow path may intersect at a 120 degree angle. In some embodiments, the flow directional control walls 308E are arranged so that the two air paths intersect the liquid flow path at about 180 degrees. The design of the flow path intersection may be different for different types of liquids, for example, a higher quality of foam may be obtained by causing the liquid soap to be intersected head on (180 degrees) by the two air flow paths, while a higher quality foam may be obtained for foamable sanitizer by having the air paths tangentially intersect with the liquid path.

FIG. 8 is a bottom view of the exemplary valve seat 308 for the foam pump 206. The valve seat 308 includes three liquid outlet apertures 309A that pass through valve seat 308 and a liquid outlet valve aperture 329A for retaining one-way liquid outlet valve 323A. Valve seat 308 also includes a liquid inlet groove 319A that extends partially into valve seat 308 to provide a liquid path from one-way liquid inlet valve 316A to the interior of liquid pump diaphragm 310A. In addition, the valve seat 308 includes a first set of three air outlet apertures 309B that pass through valve seat 308, and a second set of three air outlet apertures 309C that pass through valve seat 308. Also, valve seat 308 includes air outlet valve apertures 329B, 329C for retaining one-way air outlet valves 323B, 323C, and air inlet grooves 319B, 319C that extend partially into valve seat 308 to provide an air path from one-way air inlet valves 316B, 316C to the interior of air pump diaphragms 310B, 310C.

FIG. 9 is a top view of an exemplary diaphragm assembly seat 312 for the exemplary embodiment of a foam pump 206. The diaphragm assembly seat 312 includes three receiving holes 313A, 313B, 313C and three inlet apertures 321A, 321B, 321C. In fluid communication with inlet aperture 321A is fluid inlet 352 which may be coupled to the liquid outlet of container 102. Each receiving hole 313A, 313B, 313C is sized to receive a diaphragm 310A, 310B, 310C. Each inlet aperture 321A, 321B, 321C extends through diaphragm assembly seat 312 and allows either air, liquid soap, or sanitizer to enter one of the diaphragms 310A, 310B, 310C.

In some embodiments, the foam mixture has an air to liquid ratio of between about 7 to 1 and about 10 to 1. In some embodiments, the air to liquid ratio is greater than 10 to 1, and in some embodiments is less than 7 to 1.

In some exemplary embodiments, a flow control valve (not shown) is located between the container 102 of foamable liquid and pump 206. The flow control valve may be used to adjust the liquid to air ratio. If a higher liquid to air ratio is desired, the flow control valve is set at a lower flow rate that starves the liquid pump diaphragm 310A. Conversely, to increase the liquid to air ratio, the flow control valve may be opened wider allowing more liquid to flow into pump 206. In some embodiments, the liquid pump diaphragm 310A may have a different volume than the air pump diaphragms 310B, 310C to adjust the ratio of liquid to air. In some embodiments, the volume of the liquid pump diaphragm 310A is reduced by inserting a sponge (not shown) in the liquid pump diaphragm 310A. Not only does the sponge (not shown) reduce the volume, but in some embodiments, the sponge slows the flow of liquid through the liquid pump diaphragm 310A. In some embodiments, a restrictor comprising an orifice that has a smaller diameter than the liquid inlet may be used to restrict the fluid flow.

Figure 10A:
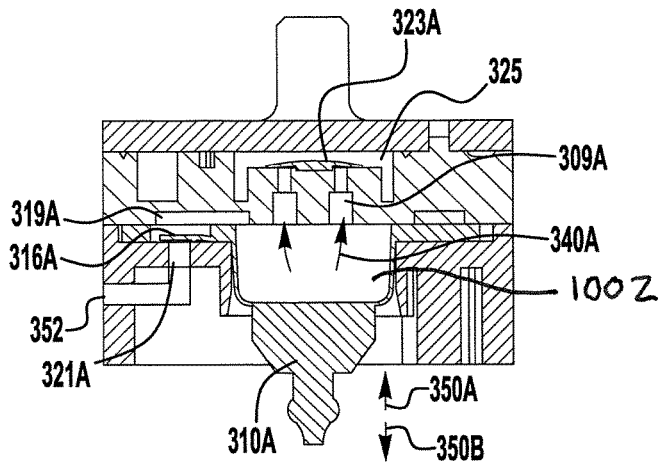
FIG. 10A is a cross-sectional view taken along the lines A-A of FIGS. 5-9 of a liquid pump portion of the sequentially activated multi-diaphragm foam pump of FIG. 3.

FIG. 10A is a cross-sectional view taken along the lines A-A of FIGS. 5-9 showing the liquid pump portion of foam pump 206. In operation, liquid pump diaphragm 310A is moved downward, as shown by reference number 350B, to expand pump chamber 1002, which causes liquid inlet valve 316A to open allowing liquid to be drawn into pump chamber 1002 through liquid inlet 352, inlet aperture 321A, and liquid inlet groove 319A. Once the pump chamber 1002 is expanded it is primed with liquid, such as, for example, liquid soap or sanitizer. When the liquid pump diaphragm 310A is compressed (i.e. the liquid pump diaphragm 310A moves in the direction shown by reference number 350A), the liquid is pumped in the direction shown by reference number 340A. The liquid travels through liquid outlet apertures 309A, past one-way liquid outlet valve 323A and into mixing chamber 325. One-way liquid outlet valve 323A is normally closed, but one-way liquid outlet valve 323A opens due to pressure caused by compressing liquid pump chamber 1002. One-way liquid outlet valve 323A prevents air or liquid from flowing back through liquid outlet apertures 309A and into liquid pump diaphragm 310A. Subsequently, the liquid pump diaphragm 310A begins to expand, which starts the process again by causing liquid inlet valve 316A to open, and liquid is drawn into liquid pump chamber 1002 through liquid inlet aperture 321A and liquid inlet groove 319A. A operating cycle of foam pump 206 includes one pump of liquid from liquid pump diaphragm 310A through liquid outlet apertures 309A, past liquid outlet valve 323A, and into mixing chamber 325 (FIG. 7) (followed by two pumps of air as described below).

Figure 10B:
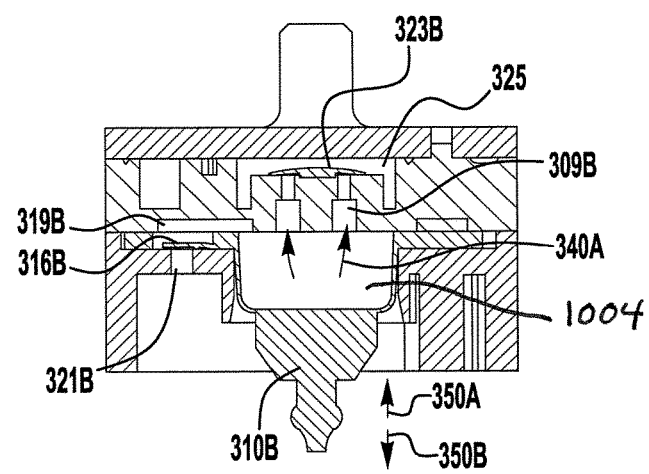
FIG. 10B is a cross-sectional view taken along the lines B-B of FIGS. 5-9 of a first air pump portion of the sequentially activated multi-diaphragm foam pump of FIG. 3.
Figure 10C:
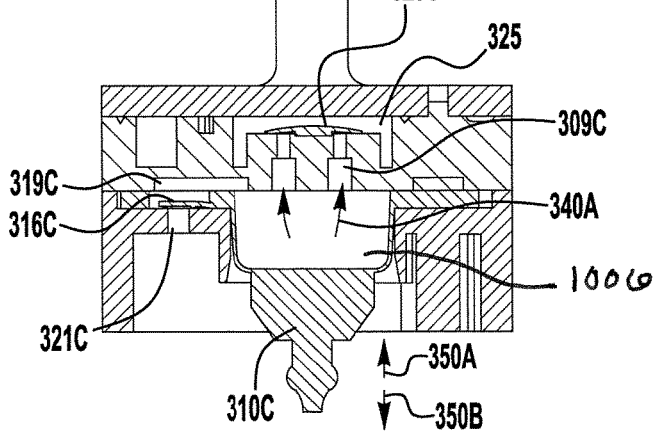
FIG. 10C is a cross-sectional view taken along the lines C-C of FIGS. 5-9 of a second air pump portion of the sequentially activated multi-diaphragm foam pump of FIG. 3.

FIGS. 10B and 10C are a cross-sectional view taken along the lines B-B and C-C, respectively, of FIGS. 5-9 showing the air pump portions of foam pump 206. In operation, air pump diaphragms 310B, 310C are moved downward, as shown by reference number 350B, to expand air pump chambers 1004, 1006, which causes air inlet valves 316B, 316C to open allowing air to be drawn into pump chambers 1004, 1006 through air inlet apertures 321B, 321C and air inlet grooves 319B, 319C. Once the pump chambers 1004, 1006 are primed with air, the air pump diaphragms 310B, 310C may be compressed (moved in the direction shown by reference number 350A). Compression of air pump diaphragms 310B, 310C pump the air in the direction shown by reference number 340A. The air travels through air outlet apertures 309B, 309C, past one-way air outlet valves 323B, 323C, and into mixing chamber 325 to mix with the foamable liquid. One-way air outlet valves 323B, 323C are normally closed, but one-way air outlet valves 323B, 323C open due to pressure caused by compressing air pump chambers 1004, 1006. One-way air inlet valves 323B, 323C prevent air or liquid from flowing back through air outlet apertures 309B, 309C and into air pump diaphragms 310B, 310C. Subsequently, the air pump diaphragms 310B, 310C begin to expand, which starts the process again by causing air inlet valves 316B, 316C to open, and air is drawn into air pump chambers 1004, 1006 through air inlet apertures 321B, 321C and air inlet grooves 319B, 319C. An operating cycle of foam pump 206 includes one pump of liquid (as described above) followed by one pump of air from air pump diaphragm 310B through air outlet apertures 309B, past air outlet valve 323B, and into mixing chamber 325 (FIG. 7). In addition, an operating cycle of foam pump 206 includes one pump of air from air pump diaphragm 310C through air outlet apertures 309C, past air outlet valve 323C, and into mixing chamber 325 (FIG. 7).

The diaphragms 310A, 310B, 310C operate sequentially, in which one sequence of operation includes one pump of liquid, such as, for example, soap or sanitizer, or air by each of the three pump diaphragms 310A, 310B, 310C. The order of operation of the pump diaphragms 310A, 310B, 310C is dependent upon the configuration of the wobble plate 314 (FIG. 3). As shown in FIG. 3, each pump diaphragm 310A, 310B, 310C has a connector 311A, 311B, 311C, and the three pump diaphragms 310A, 310B, 310C connect to the wobble plate 314 by inserting the three connectors 311A, 311B, 311C in the three wobble plate links 314A, 314B, 314C. Wobble plate 314 connects to an eccentric wobble plate actuator that causes the wobble plate 314 to undulate. As the wobble plate 314 undulates, the wobble plate links 314A, 314B, 314C move in upward and downward motions. The upward motion causes the pump diaphragms 310A, 310B, 310C to compress, and the downward motion causes the pump diaphragms 310A, 310B, 310C to expand. The configuration of the wobble plate 314 causes one pump diaphragm 310A, 310B, 310C to compress at a time, which causes the pump diaphragms 310A, 310B, 310C to pump sequentially. The configuration of the wobble plate 314 also causes one pump diaphragm 310A, 310B, 310C to expand at a time, which causes the pump diaphragms 310A, 310B, 310C to prime sequentially. In the exemplary sequence of operation, the liquid pump diaphragm 310A pumps a shot of fluid, followed by air pump diaphragm 310B pumping a shot of air, and the sequence of operation ends with air pump diaphragm 310C pumping a second shot of air. The sequence may be repeated any number of times depending on the desired output dose of foam. The air from the air pump diaphragms 310B, 310C mixes with either the liquid or sanitizer from the liquid pump diaphragm 310A in the mixing chamber 325 (FIG. 7), which creates a foam mixture. The foam mixture exits the foam pump 206 through the pump outlet 350.

FIG. 4 illustrates the flow path of the liquid soap or sanitizer through the exploded view. When the liquid pump diaphragm 310A expands, liquid enters the foam pump 206 through liquid inlet 352, which is shown by reference number 330A. The liquid travels through aperture 321A in the diaphragm assembly seat 312, and past liquid one-way inlet valve 316A, as shown by reference number 330B. Inlet valve 316A opens, the liquid travels through groove 319A and into liquid pump diaphragm 310A, which is shown by reference numbers 330D and 330E.

The liquid pump diaphragm 310A compresses and pumps the liquid through liquid outlet aperture 309A, past one-way liquid outlet valve 323A, and into the mixing chamber 325 (FIG. 7), which is shown by reference number 340A. Air follows a similar path for air pump diaphragms 310B, 310C. When air pump diaphragms 310B, 310C expand, air is drawn into air inlet 424B, travels through apertures 321B, 321C (FIG. 9) in diaphragm seat assembly 312, travels through one-way air inlet valves 316B, 316C (FIGS. 5 and 6), travels into grooves 319B, 319C, in the bottom of valve seat 308, and travels into air pump diaphragms 310B, 310C. When air pump diaphragms 310B, 310C compress, air is forced through apertures 309B, 309C, past one-way air outlet valves 323B, 323C (FIG. 7), and into mixing chamber 325 where it mixes with the liquid to form a foam mixture. The foam mixture is dispensed through outlet 350, which is shown by reference number 304B.

Figure 11:
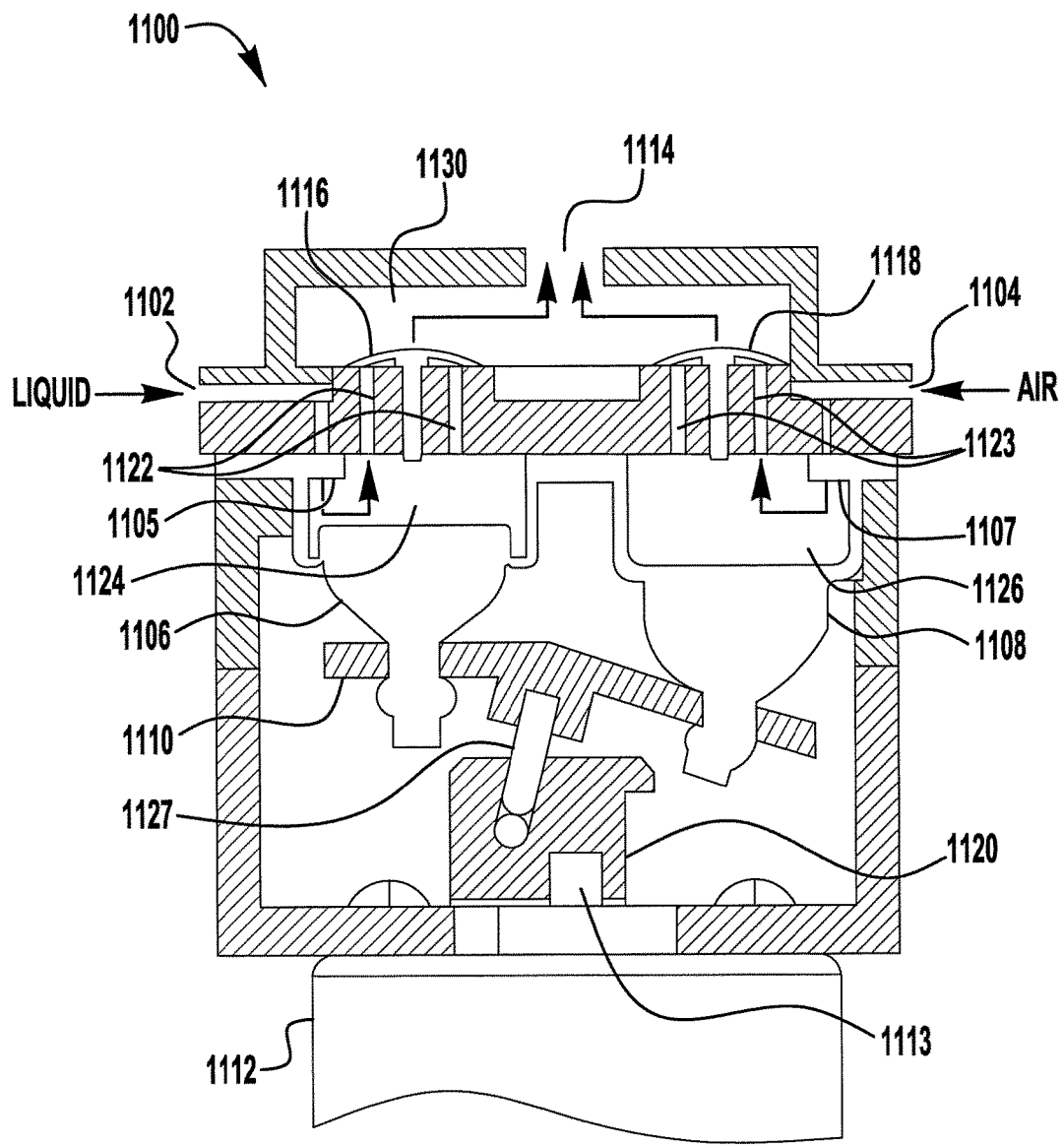
FIG. 11 is a cross-sectional view of another exemplary embodiment of a sequentially activated multi-diaphragm foam pump.

FIG. 11 is a cross-sectional view of another exemplary embodiment of a sequentially activated multi-diaphragm foam pump 1100. The sequentially activated multi-diaphragm foam pump 1100 includes a motor 1112, a motor shaft 1113, a wobble plate 1110, a wobble plate pin 1127 an eccentric wobble plate drive 1120, a liquid pump diaphragm 1106, two air pump diaphragms 1108 (only one is shown), mixing chamber 1130, and pump outlet 1114. The motor 1112 drives the motor shaft 1113, which causes the motor shaft 1113 to rotate. The rotation of the motor shaft 1113 causes the eccentric wobble plate drive 1120 to rotate, and rotation of the eccentric wobble plate drive 1120 causes the wobble plate pin 1127 to move along a circular path, which causes the wobble plate 1110 to undulate. In some embodiments, wobble plate 1110 includes a ball (not shown) that rides in a socket (not shown) on the pump housing and wobble plate pin 1127 extends outward and connects to an eccentric wobble plate actuator 1120 that causes the pin to move along a circular path which causes the wobble plate 1110 to undulate. As the wobble plate 1110 undulates, the ends connected to the three pump diaphragms 1106, 1108 move in upward and downward motions, and the three pump diaphragms 1106, 1108 are compressed sequentially. One sequence of operation of the mixing pump 1100 includes one pump by each of the three pump diaphragms 1106, 1108.

The liquid pump diaphragm 1106 operates first in the cycle of operation, followed by sequential distributions by the two air pump diaphragms 1108.

Similar to the embodiments described above, during operation, the liquid pump diaphragm 1106 expands and contracts to pump liquid, and the air pump diaphragms 1108 (only one is shown) expand and contract to pump air. The expansion of the liquid pump diaphragm 1106 opens the liquid inlet valve 1105 and allows liquid, such as, for example, soap or sanitizer to enter liquid pump chamber 1124 through liquid inlet 1102. The expansion of the air pump diaphragms 1108 opens the air inlet valves 1107 (only one is shown) and allows air to enter air pump chambers 1126 (only one is shown) through air inlets 1104. Circular movement of the wobble plate pin 1127 causes the ends of the wobble plate 1110 to sequentially undulate. The undulation causes liquid pump diaphragm to compress, which causes liquid outlet valve 1116 to open, and liquid to flow into the mixing chamber 1130 through liquid outlet apertures 1122. Subsequently, one of the air pump diaphragms 1108 is compressed by the undulating wobble plate 1110, which causes air outlet valve 1118 to open, and air to flow the mixing chamber 1130 through air outlet apertures 1123. Then, the other air pump diaphragm (not shown) will compress and pump air into mixing chamber 1130. The air and liquid soap or sanitizer mix in the mixing chamber 1130 to create a foam mixture. The foam mixture exits the mixing pump 1100 through pump outlet 1114.

Figure 12:
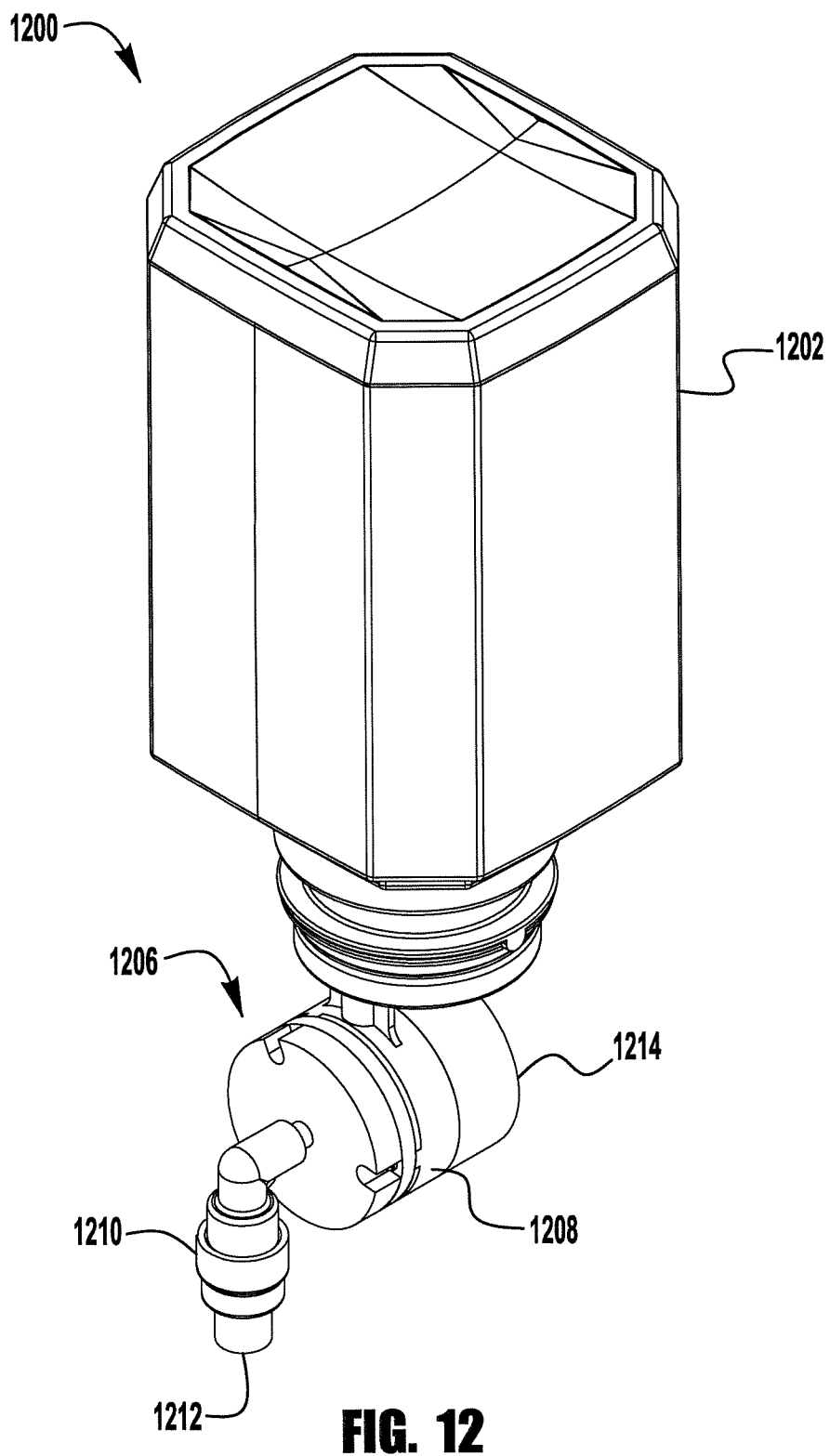
FIG. 12 is a perspective view of an exemplary embodiment of a refill unit having a sequentially activated multi-diaphragm foam pump.
Figure 13:
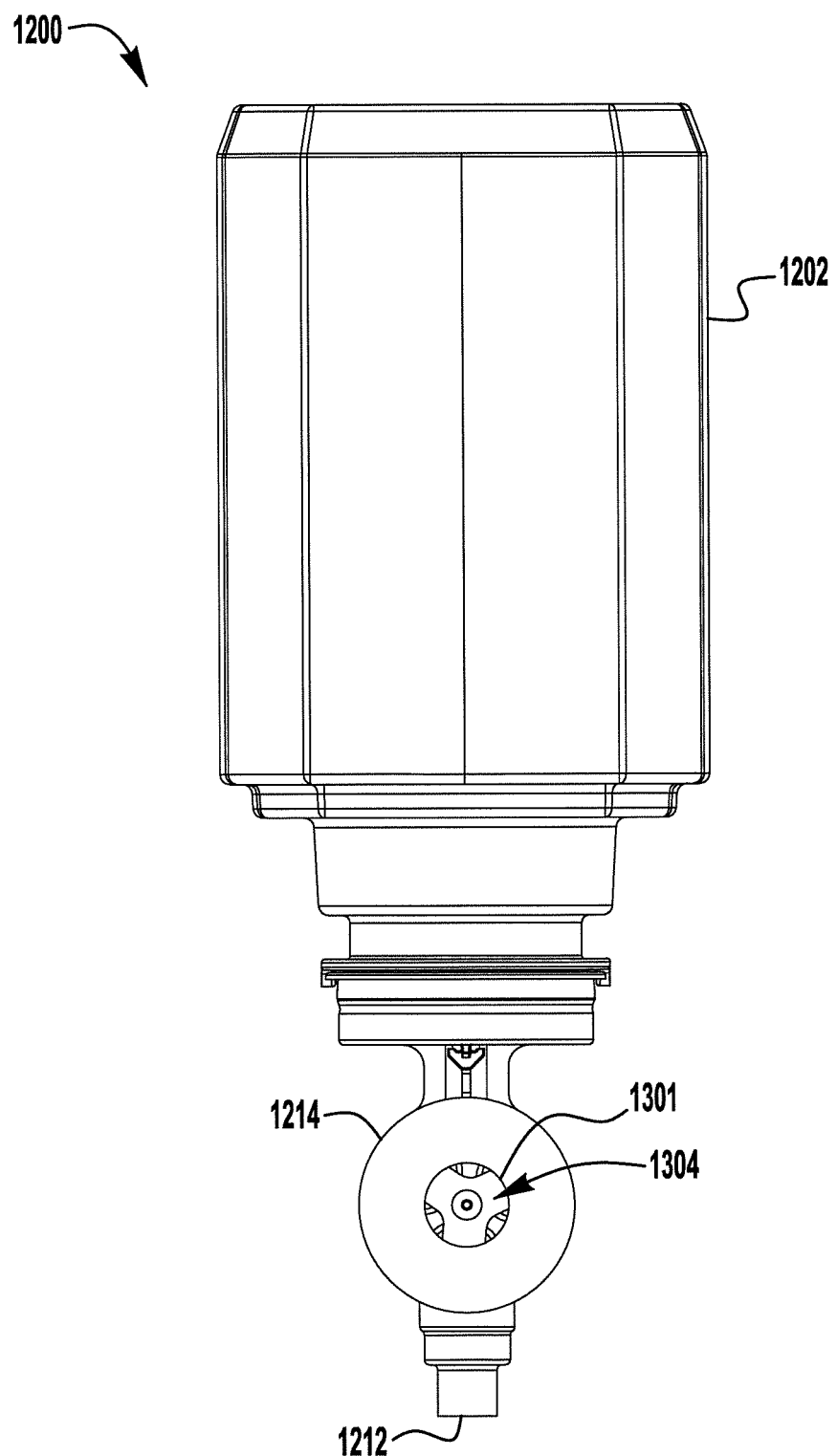
FIG. 13 is a rear view of the exemplary embodiment of the refill unit having a sequentially-activated multi-diaphragm foam pump of FIG. 12 with a back cover.
Figure 14:
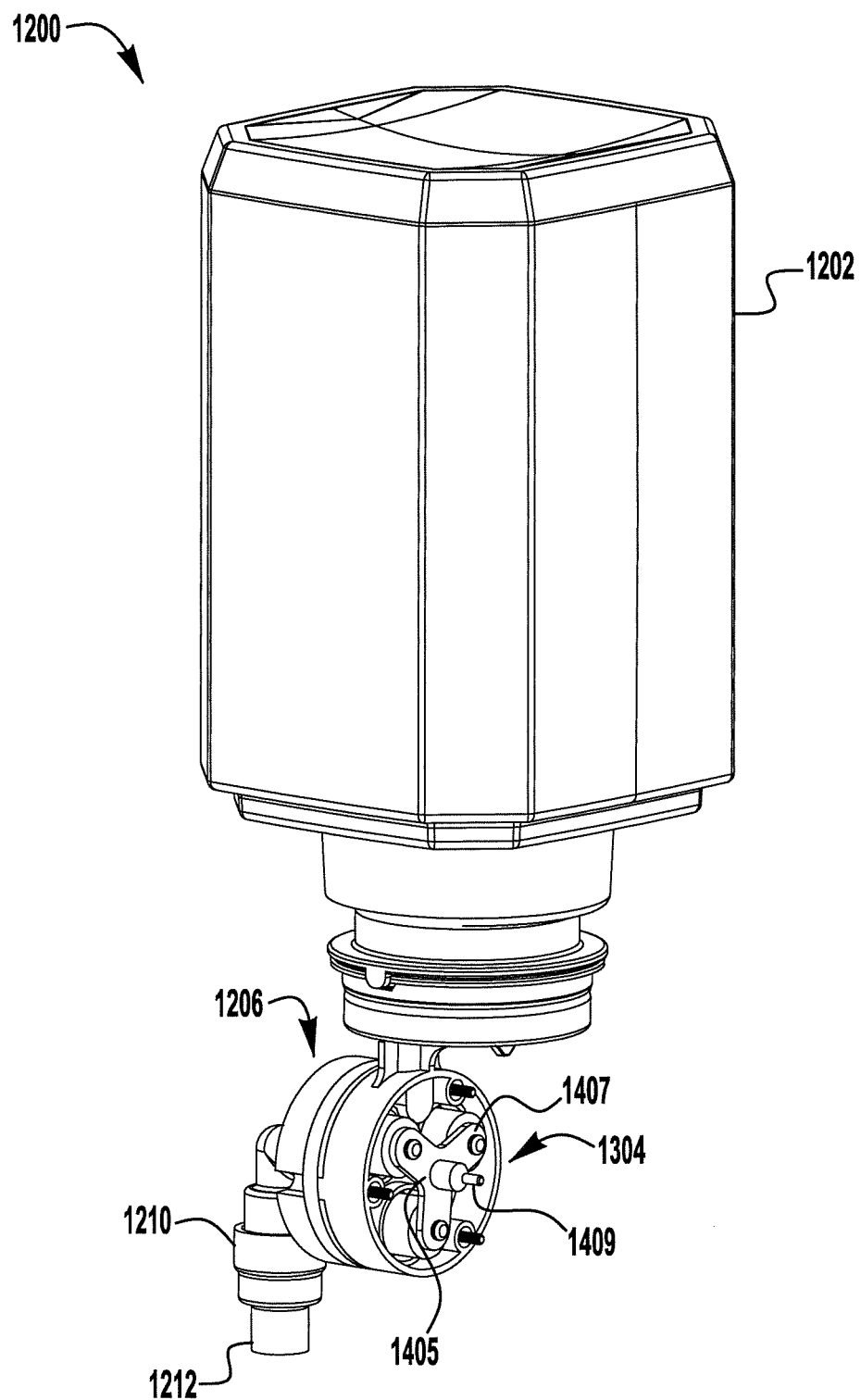
FIG. 14 is a perspective view of the exemplary embodiment of the refill unit having a sequentially-activated multi-diaphragm foam pump of FIG. 12 without the back cover.
Figure 15:
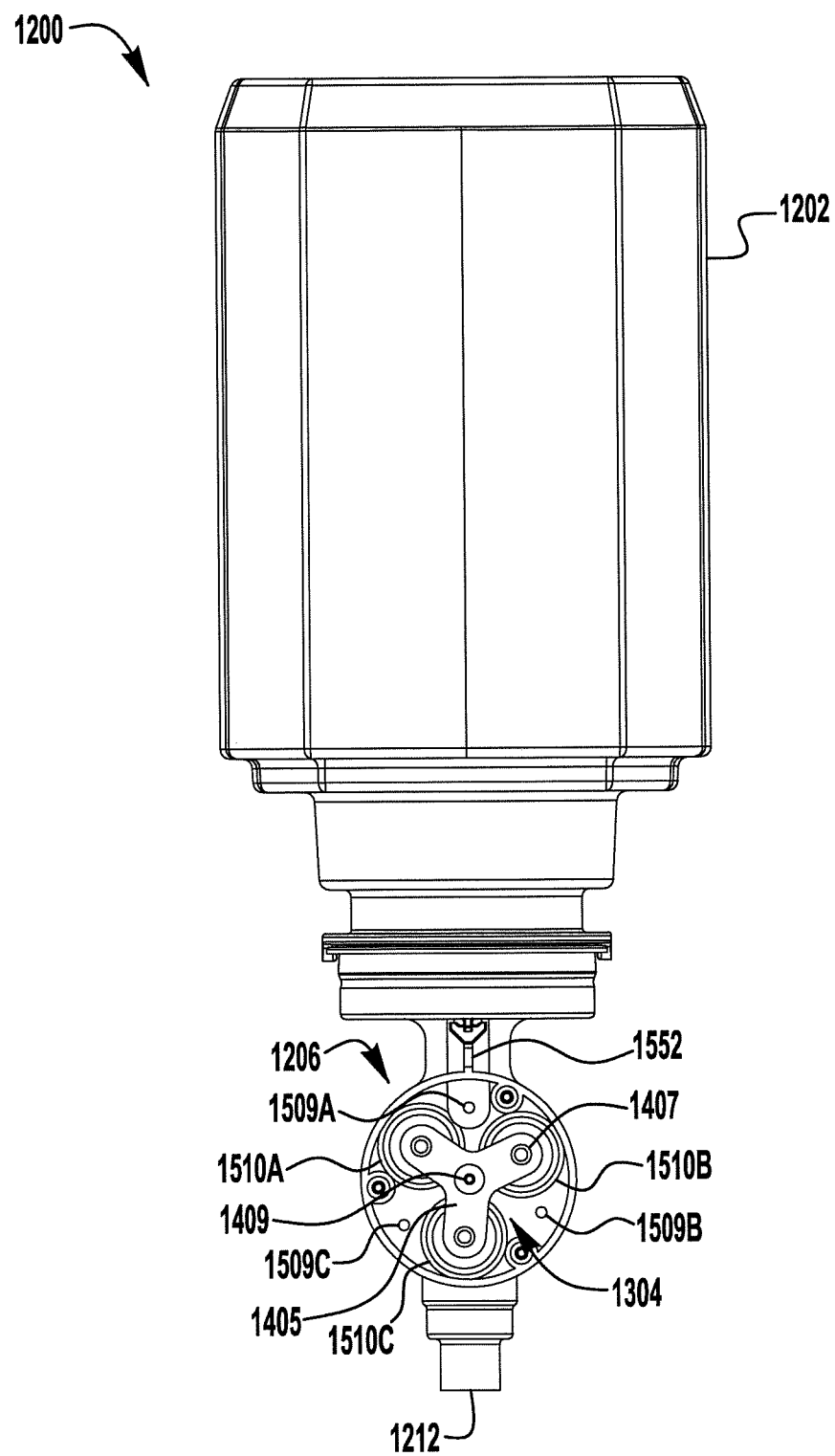
FIG. 15 is a back view of the exemplary embodiment of the refill unit having a sequentially-activated multi-diaphragm foam pump of FIG. 12 without the back cover.
Figure 16:
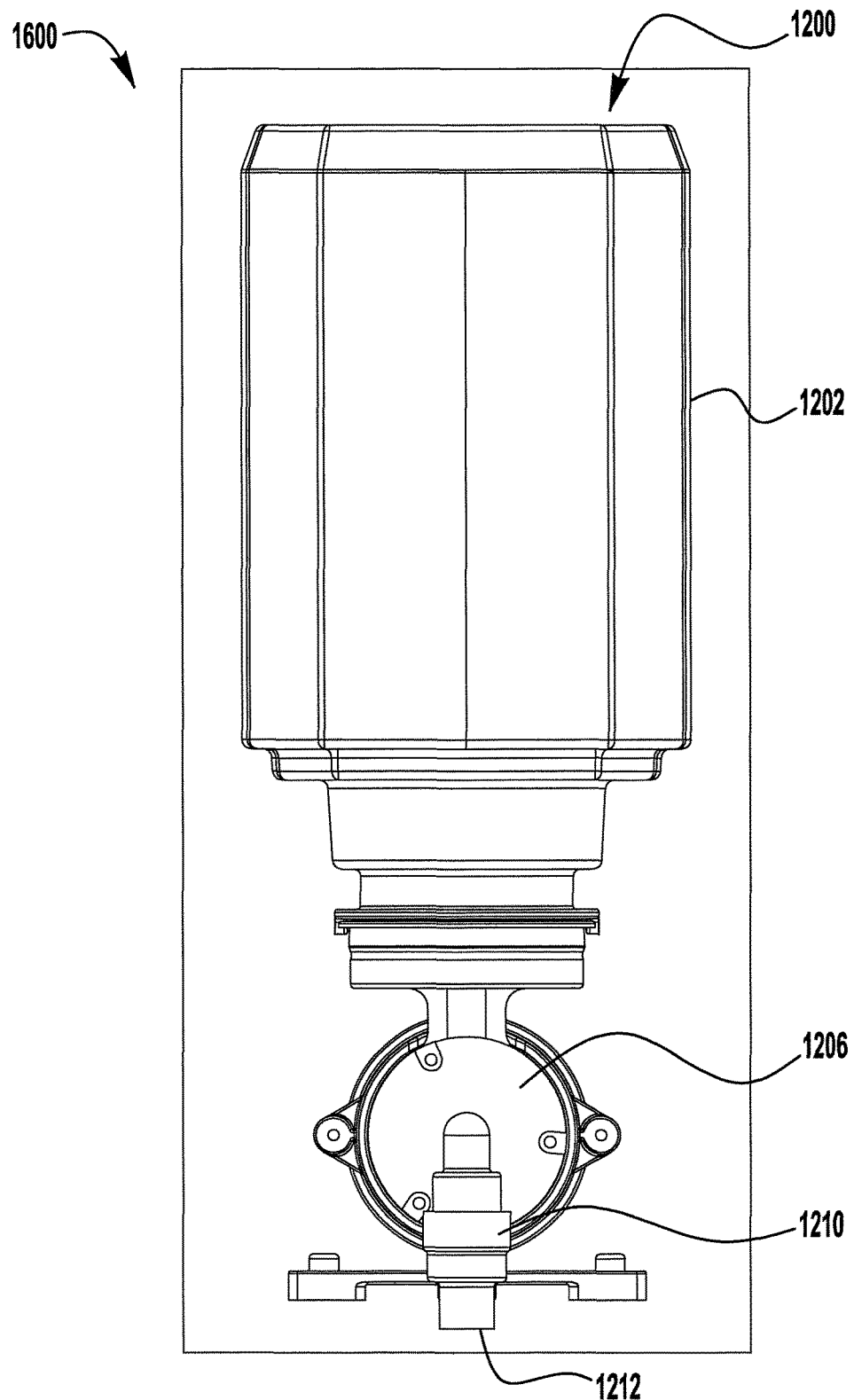
FIG. 16 is an exemplary foam dispenser with the refill unit having a sequentially-activated multi-diaphragm foam pump installed therein.
Figure 17:
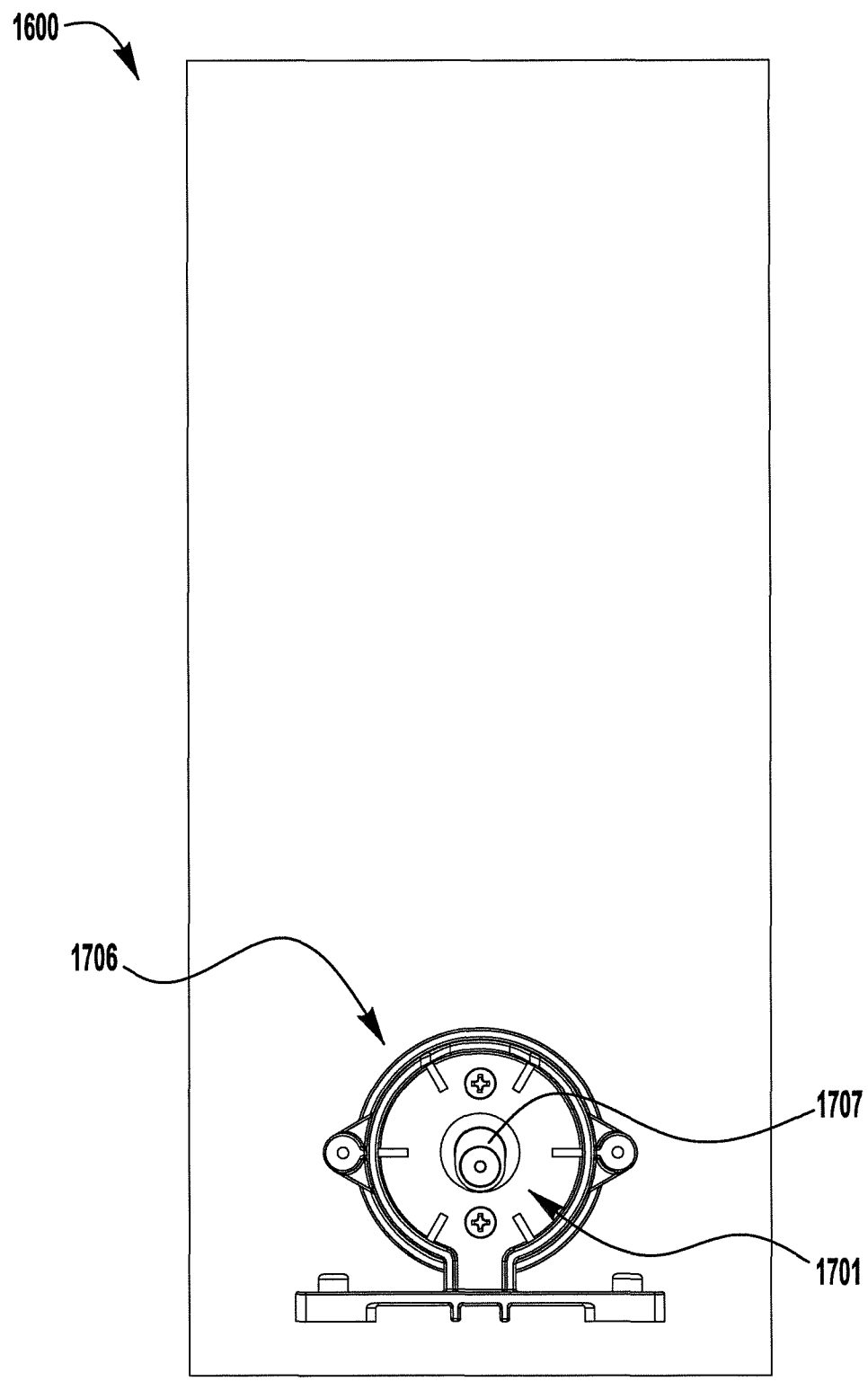
FIG. 17 is the exemplary foam dispenser with the refill unit removed.

FIGS. 12-15 illustrate and exemplary embodiment of a refill unit 1200. FIG. 12 is a perspective view of an exemplary embodiment of a refill unit 1200 having a sequentially activated multi-diaphragm foam pump 1206, and FIG. 13 is another perspective view of the exemplary refill unit 1200, having a back plate 1214 removed to illustrate the plurality of diaphragms 1510A, 1510B and 1510C. FIG. 13 is a rear elevational view of the refill unit 1200 and FIG. 15 is a rear elevational view of the refill unit 1200 with the back plate 1214 removed to illustrate the plurality of diaphragms 1510A, 1510B and 1510C. The refill unit 1200 connects to a foam dispenser 1600 (FIGS. 16, 17). The refill unit 1200 includes a container 1202, a foam pump 1206, a actuation mechanism 1304 (FIG. 13), a foam cartridge 1210, and a nozzle 1212. Refill unit 1200 contains a supply of a foamable liquid. In various embodiments, the contained foamable liquid could be for example a soap, a sanitizer, a cleanser, a disinfectant, a lotion or the like. The container 1202 is a collapsible container and can be made of thin plastic or a flexible bag-like material. In some embodiments, the container 1202 is a non-collapsing container formed by a rigid, or semi-rigid housing member, or any other suitable configuration for containing the foamable liquid without leaking. In the case of a non-collapsing container, a vent system may be included, such as, for example, any of the venting systems in the patents/application incorporated above.

Foam pump 1206, is similar to the pumps described above, and includes a housing 1208, a liquid pump diaphragm 1510A (FIG. 15), air pump diaphragms 1510B, 1510C, and a mixing chamber (not shown). The liquid pump diaphragm 1510A and the air pump diaphragms 1510B, 1510C are disposed in housing 1208. The liquid pump diaphragm 1510A receives liquid from the container 1202 through liquid inlet 1552 and liquid inlet apertures 1509A, and liquid pump diaphragm 1510A pumps the liquid into the mixing chamber. The air pump diaphragms 1510B, 1501C receive air through at least one air inlet (not shown) and air inlet apertures 1509B, 1509C, and air pump diaphragms 1510B, 1510C pump the air into the mixing chamber. The liquid pump diaphragm 1510A and the air pump diaphragm 1510B are sequentially activated by actuation mechanism 1304 (FIG. 13). An operating cycle of the foam pump 1206 includes one pump of liquid from liquid pump diaphragm 1510A into mixing chamber 325 and one pump of air from air pump diaphragms 1510B, 1510C into the mixing chamber. The operating cycle begins with the one shot of liquid from liquid pump diaphragm 1510A, which is followed by the one shot of air form air pump diaphragm 1510B and one shot of air from air pump diaphragm 1510C. The liquid and air mix in mixing chamber (not shown) to form a foamy mixture, and the foamy mixture passes through foam cartridge 1210 and exits the foam pump 1206 through the outlet 1212. A dispense of foam typically requires one or more operating cycles or revolutions. In some embodiments of the present invention, the foam mixture has an air to liquid ratio of between about 7 to 1 and about 10 to 1. In some embodiments, the air to liquid ratio is greater than 10 to 1, and in some embodiments is less than 7 to 1.

In some exemplary embodiments, a flow control valve (not shown) is located between the container 1202 of foamable liquid and pump 1206. The flow control valve may be used to adjust the liquid to air ratio. If a higher liquid to air ratio is desired, the flow control valve is set at a lower flow rate that starves the liquid pump diaphragm 1510A. Conversely, to increase the liquid to air ratio, the flow control valve may be opened wider allowing more liquid to flow into pump 1206. In some embodiments, the liquid pump diaphragm 1510A may have a different volume than the air pump diaphragms 1510B, 1510C to adjust the ratio of liquid to air. In some embodiments, the volume of the liquid pump diaphragm 1510A is reduced by inserting a sponge (not shown) in the liquid pump diaphragm 1510A. Not only does the sponge (not shown) reduce the volume, but in some embodiments, the sponge slows the flow of liquid through the liquid pump diaphragm 1510A.

The foam pump 1206 may include some or all of any of the embodiments described herein. Moreover, the foam pump 1206 may have more than one liquid pump diaphragm and one or more air pump diaphragms.

The actuation mechanism 1304 (FIG. 13) releasably connects to a drive system of motor 1706 (FIG. 17) that is permanently attached to a foam dispenser 1600. Actuation mechanism 1304 is covered by back plate 1214.

In some embodiments, the actuation mechanism 1304 does not include a wobble plate 1405, but may include a circular plate (not shown) and one or more springs (not shown). The circular plate is connected to the liquid pump diaphragm 1510A and the air pump diaphragms 1510B, 1510C. The one or more springs bias the circular plate outward thereby urging the liquid pump diaphragm 1510A and the air pump diaphragms 1510B, 1510C to their extended position. The drive system (not shown) on the dispenser includes a wheel that travels around the perimeter of the circular plate. The point of contact between the wheel and the circular plate pushes that portion of the circular plate downward. As the wheel rotates around the perimeter it sequentially compresses the liquid pump diaphragm 1510A and the air pump diaphragms 1510B, 1510C. As the wheel moves past the diaphragms 1510A, 1510B, 1510C, the diaphragms 1510A, 1510B, 1510C expand to draw in fluid, as they are biased toward the expanded position by the diaphragm material as well as the one or more springs. In some embodiments, the springs are not needed and the diaphragm material is sufficient to bias the diaphragms 1510A, 1510B, 1510C to their expanded positions.

The above-mentioned embodiments are only exemplary, and the actuation mechanism 1304 may be configured in any manner that causes sequential operation of the liquid pump diaphragm 1510A and air pump diaphragms 1510B, 1510C of foam pump 1206.

FIG. 13 is a back view of the exemplary embodiment of the refill unit 1200 having a sequentially-activated multi-diaphragm foam pump 1206 of FIG. 12 with back plate 1214. Back plate 1214 has an aperture 1301. The refill unit 1200 attaches to a foam dispenser 1600 (FIG. 16) by connecting the attachment mechanism 1304 to the drive system of motor 1706 through the aperture 1301 of back plate 1214.

Figure 18:
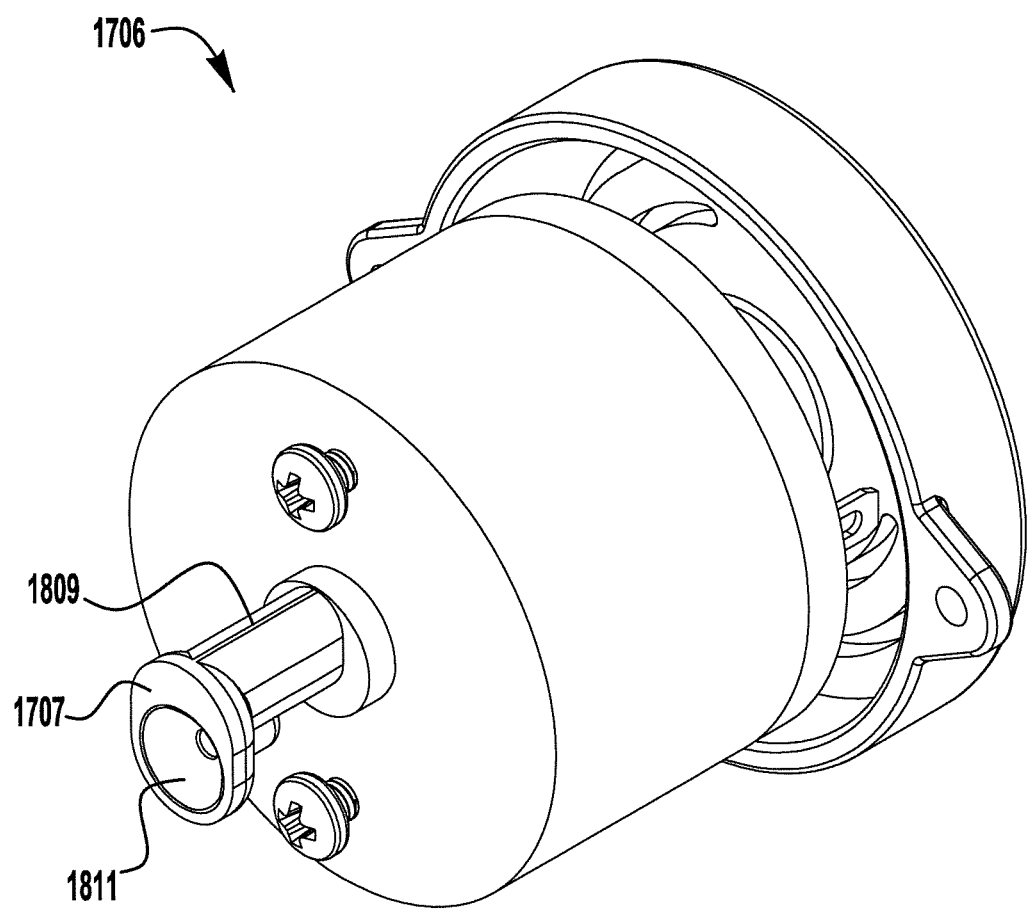
FIG. 18 is an exemplary motor and drive system for the exemplary foam dispenser of FIG. 16.

FIGS. 14 and 15 are views of the exemplary embodiment of the refill unit 1200 having the sequentially-activated multi-diaphragm foam pump 1206 with the back plate 1214 removed. The actuation mechanism 1304 includes a wobble plate 1405, wobble plate connection links 1407, and pin 1409. Each wobble plate link 1407 connects to pump diaphragms 1510A, 1510B, 1510C. In this exemplary embodiment, the pin 1409 of actuation mechanism 1304 releasably connects the actuation mechanism 1304 to an eccentric drive system 1707 (FIGS. 17 and 18) of motor 1706. Referring to FIGS. 17 and 18, a portion of pump 1206 of refill unit 1200 is received in socket 1701 of foam dispenser 1600, and the actuation mechanism 1304 releasably connects to the eccentric drive system 1707. Eccentric drive system 1707 is attached to shaft 1809 of motor 1706. The pin 1409 of actuation mechanism 1304 releasably engages with eccentric drive system 1707 pin 1409 engaging notch 1811. In some embodiments, the eccentric drive system 1707 is connected to actuation mechanism 1304 and is part of the refill unit 1200 and releasably connects to the shaft 1809 of motor 1706. The above-mentioned embodiments are only exemplary. The refill unit 1200 and motor 1706 may be configured in any manner that allows the refill unit 1200 to releasably attach to motor 1706 and allows motor 1706 to operate foam pump 1206.

Referring to FIGS. 14 and 15, the eccentric drive system 1707 (FIGS. 17 and 18) causes the wobble plate 1405 to undulate, which causes sequential operation of the liquid pump diaphragm 1510A and air pump diaphragms 1510B, 1510C. As the liquid pump diaphragm 1510A expands, liquid travels from container 1202, through liquid inlet 1552 and liquid inlet aperture 1509A, and into liquid pump diaphragm 1510A. The liquid pump diaphragm 1510A is in a primed position when it is filled with liquid. As air pump diaphragms 1510B, 1510C expand, air travels through at least one air inlet (not shown), through air inlet apertures 1509B, 1509C, and into respective air pump diaphragms 1510B, 1510C. The air pump diaphragms 1510B, 1510C are in primed positions when they are filled with air. An exemplary operating cycle includes one pump of liquid from liquid pump diaphragm 1510A, followed by one pump of air from air pump diaphragm 1510B, followed by one pump of air from air pump diaphragm 1510C.

In some embodiments, each pump diaphragm 1510A, 1510B, 1510C has a volume between about 0.1 and 1.0 ml. The pump diaphragms 1510A, 1510B, 1510C pump liquid and air into a mixing chamber (not shown), and the liquid and air mix to form a foamy mixture. The foamy mixture goes through a foam cartridge 1210 to form a rich foam, and the rich foam exits the refill unit 1200 through nozzle 1212. In some embodiments the liquid pump diaphragm 1510A has a volume of between about 0.1 and 1.0 ml.

In some embodiments the dose of foam dispensed by the foam dispenser contains between about 0.3 ml and about 7.0 ml of liquid of liquid. In some embodiments, the dose of foam comprises between about 3 and 10 revolutions per dispense, including between about 3 and 7 revolutions, including between about 5 and 10 revolutions. In some embodiment, the dose of foam is about 0.3 ml for a highly concentrated light duty soap. In some embodiments, the dose of foam is about 7.0 ml of liquid for heavy duty soaps, such as grease cleaning soaps.

In some embodiments, the dispenser operates at a voltage of between about 3 volts and 10 volts, including between about 3 volts and about 5 volts, including between about 4 and about 6 volts, including between about 4 volts and 8 volts, including between about 6 volts and about 9.5 volts.

In some embodiments, the pump sequences for between about 0.3 and 2 seconds to dispense a dose of foam, including between about 0.5 seconds and 1.5 seconds, including between about 0.5 and 1 seconds. In some embodiments, such as, for example, dispensing of foam sanitizer having about 1.2 ml of liquid, the dispense time is about 0.6 sec. In some embodiments, such as, for example, light duty and heavy duty soap having between about 0.3 ml liquid to about 7.0 ml liquid, the dispense time in less than 1.50 sec.

In some embodiments, the wobble plate drive actuator rotates at between about 120 and about 480 revolutions per minute.

In some embodiments, there are multiple liquid pump diaphragms, such as for example, two liquid pump diaphragms, three liquid pump diaphragms, four liquid pump diaphragms. In some embodiments there are multiple air pump diaphragms, for example, two air pump diaphragms, three air pump diaphragms, four air pump diaphragms, five air pump diaphragms, six air pump diaphragms, seven air pump diaphragms and eight. air pump diaphragms. In some embodiments, the number of air pump diaphragms to liquid pump diaphragms is 1:1, 2:1, 3:1, 4:1, 5:1, 6:1, 7:1, and 8:1.

FIGS. 19A-19B, 20A-20B, and 21A-21E illustrate various views of another exemplary embodiment of a sequentially-activated multi-diaphragm foam pump 1900. The foam pump 1900 is coupled to foam cartridge housing 1902 and container receiver 1904, and the foam cartridge housing 1902 is coupled to a nozzle 1906. The foam pump 1900 includes housing 1908, diaphragm assembly 1910, pump outlet 1912, and pump cover 1914. The diaphragm assembly 1910 includes three pump diaphragms 1916a, 1916b, 1916c. The three pump diaphragms 1916a, 1916b, 1916c include one liquid pump diaphragm 1916a and two air pump diaphragms 1916b, 1916c. The diaphragm assembly 1910 is only exemplary, and a diaphragm assembly 1910 may include more than three pump diaphragms. Additionally, the diaphragm assembly may include one or more liquid pump diaphragms and/or one or more air pump diaphragms.

A container (not shown) is connected to container with closure 1904 in a manner that allows liquid to enter liquid inlet 1918. During operation, when liquid pump diaphragm 1916a expands, liquid is drawn through liquid channel 1920, past liquid inlet valve 1922a, and into the liquid pump diaphragm 1916a. Similarly, when air pump diaphragms 1916b, 1916c expand, air is drawn through an opening, past air inlet valves 1922b, 1916c, and into the air pump diaphragms 1916b, 1916 c respectively. When the liquid pump diaphragm 1916a compresses, liquid is forced out of liquid pump diaphragm 1916a and causes the wall of liquid outlet valve 1923, which is normally closed due to the natural resiliency of the member, to deflect away from side wall 1927 and the liquid flows into mixing chamber 2132 (FIG. 21E). Similarly, as the air pump diaphragms compress, air is forced out of air pump diaphragms 1916b, 1916c and causes the wall of liquid outlet valve 1923 to deflect away from side wall 1927 and the air flows into mixing chamber 2132. When pressure from the liquid or air is removed, e.g. when the liquid pump diaphragm 1916a or the air pump diaphragms 1916b, 1916c expand, liquid outlet valve 1923 seals against side wall 1927 and seals off the diaphragms 1916a, 1916b, 1916c from the outlet nozzle 1906.

The liquid and air mix in a mixing chamber 2132 to create a foam mixture, and the foam mixture exits pump outlet 1912. After the foam mixture exits pump outlet 1912, the foam mixture travels through foam cartridge 1924. In this particular embodiment, foam cartridge 1924 includes screens 1926a, 1926b and sponge 1928. The foam cartridge 1924 may include various members, for example, foam cartridge 1924 members may include one or more screens 1926 and/or one or more sponges 1928. The foam exits the foam cartridge 1924 and is dispensed out of outlet nozzle 1906 as rich foam.

The pump diaphragms 1916a, 1916b, 1916c operate sequentially, and the operation of the pump diaphragms 1916a, 1916b, 1916c may take any form as described for the various embodiments of foam pumps described herein. In one embodiment, the liquid pump diaphragm 1916a operates first in an operating cycle, followed by sequential operation by the two air pump diaphragms 1916b, 1916c.

Figure 22:
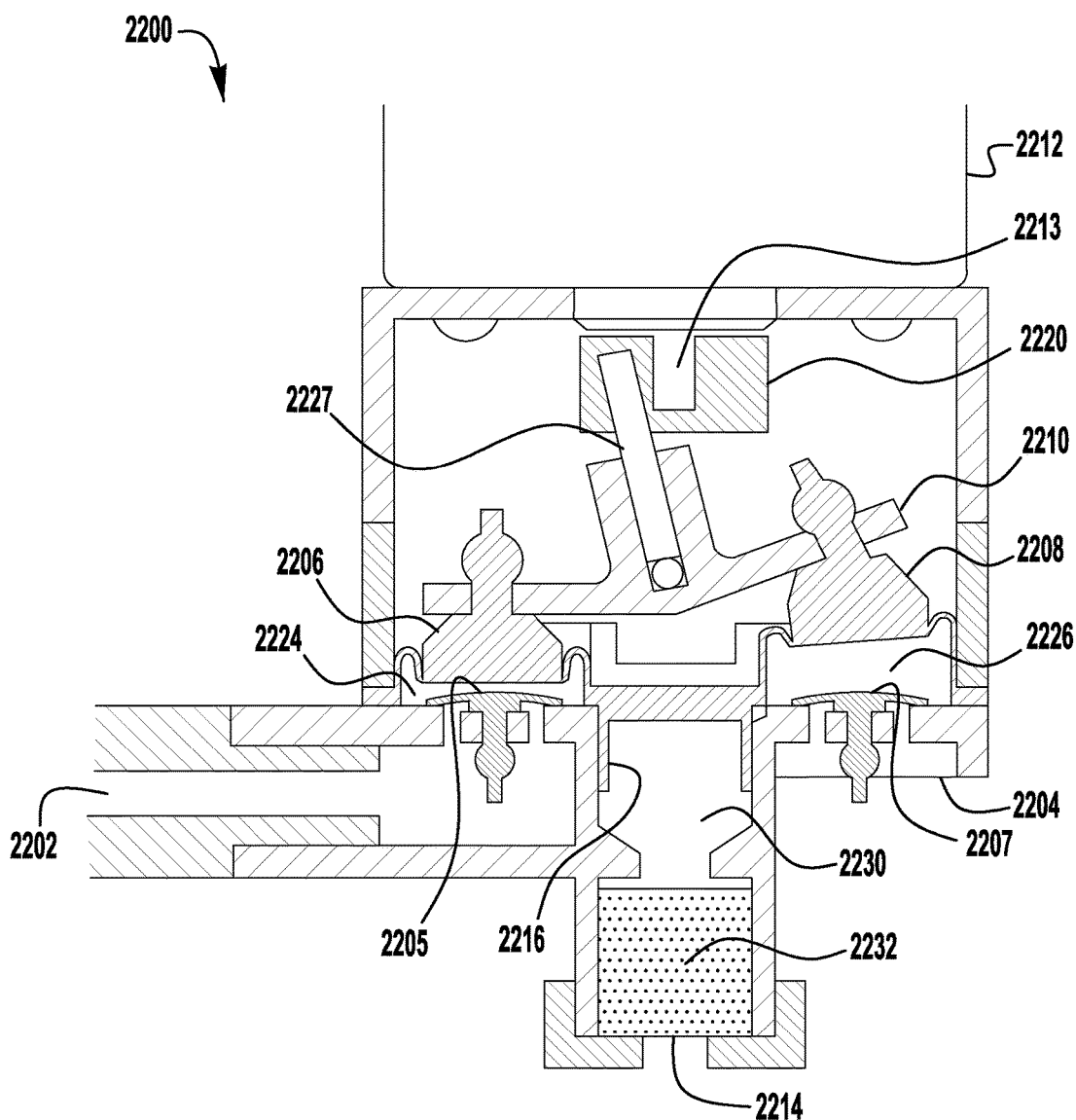
FIG. 22 is a cross-sectional view another exemplary embodiment of a sequentially-activated multi-diaphragm foam pump.

FIG. 22 is a cross-sectional view of another exemplary embodiment of a sequentially-activated multi-diaphragm foam pump 2200. The sequentially activated multi-diaphragm foam pump 2200 is driven by a motor 2212 that has a motor shaft 2213. The foam pump 2200 includes a wobble plate 2210, a wobble plate pin 2227 an eccentric wobble plate drive 2220, a liquid pump diaphragm 2206, two air pump diaphragms 2208 (only one is shown), mixing chamber 2230, liquid inlet 2202, liquid inlet valve 2205, air pump chamber 2226, air inlet 2204, air inlet valve 2207, outlet valve 2216, mixing chamber 2230 and outlet 2214.

The motor 2212 drives the motor shaft 2213, which causes the motor shaft 2213 to rotate. The rotation of the motor shaft 2213 causes the eccentric wobble plate drive 2220 to rotate, and rotation of the eccentric wobble plate drive 2220 causes the wobble plate pin 2227 to move along a circular path, which causes the wobble plate 2210 to undulate. In some embodiments, wobble plate 2210 includes a ball (not shown) that rides in a socket (not shown) on the pump housing and wobble plate pin 2227 extends outward and connects to an eccentric wobble plate actuator 2220 that causes the pin to move along a circular path which causes the wobble plate 2210 to undulate. As the wobble plate 2210 undulates, the ends connected to the three pump diaphragms 2206, 2208, move in upward and downward motions, and the three pump diaphragms 2206, 2208 are expanded and compressed sequentially.

Expansion of the liquid pump diaphragm 2206 causes the liquid inlet valve 2205 to open and draws liquid, such as, for example, soap or sanitizer into liquid pump chamber 2224 through liquid inlet 2202. Expansion of the air pump diaphragms 2208 (only one is shown) causes the air inlet valves 2207 to open (only one is shown) and draw air into air pump chambers 2226 through air inlets 2204 (only one is shown). Compression of the liquid pump diaphragm 2206 causes liquid pump chamber 2224 to compress, which causes outlet valve 2216 to deflect and open, and causes liquid to flow into the mixing chamber 2230. Compression of one of the air pump diaphragms 2208 causes air pump chamber 2226 to compress, which causes outlet valve 2216 to deflect away from the side wall and open to allow air to flow the mixing chamber 2230. The second air pump diaphragm similarly pumps air into the mixing chamber. The air and liquid soap or sanitizer mix in the mixing chamber 2230 to create a foam mixture. The foam mixture travels through foam cartridge 2232 and exits the foam pump 2200 through pump outlet 2214.

One sequence of operation of the foam pump 2200 includes one pump by each of the three pump diaphragms 2206, 2208. The liquid pump diaphragm 2206 operates first in the cycle of operation, followed by sequential distributions by the two air pump diaphragms 2208.

Figure 23:
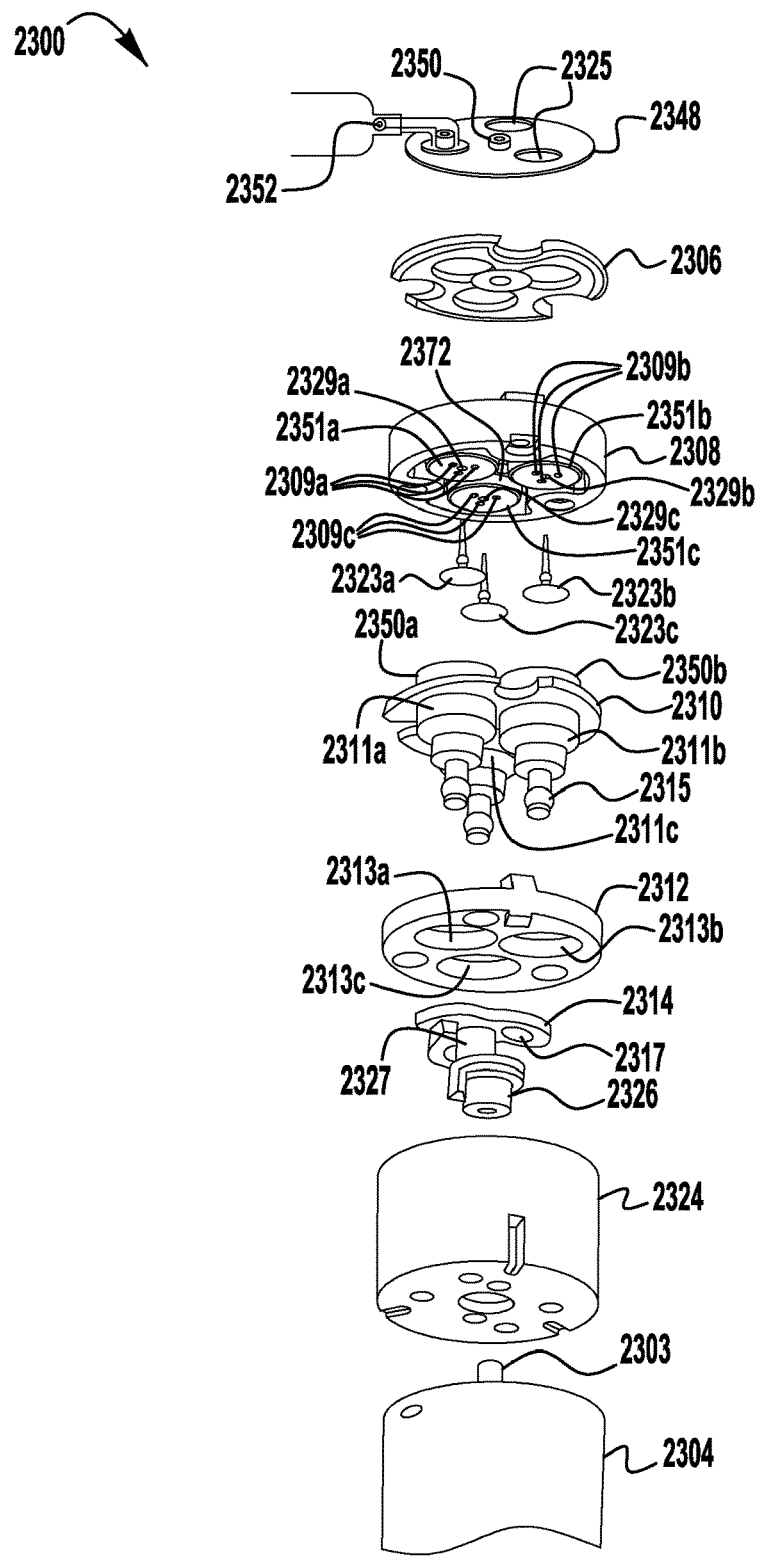
FIG. 23 is an exploded view of another exemplary embodiment of a sequentially-activated multi-diaphragm foam pump.

FIG. 23 is an exploded view of another exemplary embodiment of a sequentially-activated multi-diaphragm foam pump 2300. Foam pump 2300 is driven by motor 2304. Foam pump 2300 includes a pump housing 2324, a wobble plate 2314, a diaphragm assembly seat 2312, a diaphragm assembly 2310, a valve seat 2308, inlet valves 2323a, 2323b, 2323c a gasket 2306, and a cover 2348. The cover 2348 is attached to the valve seat 2308, and the gasket 2306 is located between the cover 2348 and gasket 2306 forms a seal around air inlet apertures 2325, liquid inlet 2352 and foam outlet 2350 to prevent fluid leaks. Inlet valves 2323a, 2323b, 2323c are secured to and seated in the valve seat 2308.

The diaphragm assembly 2310 includes three pump diaphragms 2311a, 2311b, 2311c, and each pump diaphragm 2311a, 2311b, 2311c has a connector 2315 The diaphragm assembly 2310 sits in the diaphragm assembly seat 2312. The pump diaphragms 2311a, 2311b, 2311c, are disposed in the receiving holes 2313a, 2313b, 2313c respectively, of the diaphragm assembly seat 2312, and the three connectors 2315 connect to the wobble plate 2314 by inserting the three connectors 2315 into three respective wobble plate links 2317.

The bottom of valve seat 2308 has three cylindrical projections 2351a, 2351b, 2351c that correspond to the three pump diaphragms 2311a, 2311b, 2311c respectively. The three pump diaphragms 2311a, 2311b, 2311c fit snugly over the three cylindrical projections 2351a, 2351b, 2351c and perform the function of one-way liquid outlet valves. When pump diaphragms 2311a, 2311b, 2311c expand and the interior of the pump diaphragms 2311a, 2311b, 2311c are under negative pressure, the pump diaphragms 2311a, 2311b, 2311c seal against the wall of cylindrical projections 2351a, 2351b, 2351c, respectively, and prevent the flow of fluid into the pump diaphragms 2311a, 2311b, 2311c from between the pump diaphragms 2311a, 2311b, 2311c and the wall of cylindrical projections 2351a, 2351b, 2351c. When pump diaphragms 2311a, 2311b, 2311c compress and the interior of the pump diaphragms 2311a, 2311b, 2311c are under positive pressure, the pump diaphragms 2311a, 2311b, 2311c flex away from the wall of cylindrical projections 2351a, 2351b, 2351c, respectively, and allow fluid to flow out of the pump diaphragms 2311a, 2311b, 2311c. When the positive pressure stops, or is below the cracking pressure of the pump diaphragms 2311a, 2311b, 2311c, the pump diaphragms 2311a, 2311b, 2311c move back to their normal position and form a seal against wall of cylindrical projections 2351a, 2351b, 2351c. In addition, each cylindrical projections 2351a, 2351b, 2351c has one or more fluid inlet apertures 2309a, 2309b, 2309c that extend through valve seat 2308 and a valve stem retention aperture 2329a, 2329b, 2329c respectively.

Similar to the embodiments described above, during operation, when liquid pump diaphragm 2311a expands, a vacuum is crated and liquid is drawn in through liquid inlet 2352, through fluid inlet apertures 2309a, past fluid inlet valve 2323a and into liquid pump diaphragm 2311a. Similarly, when air pump diaphragms 2311b, 2311c expand, air is drawn in through air inlets 2325, through air inlet apertures 2309b, 2309c, past fluid inlet valves 2323b, 2323c and into air pump diaphragms 2311b, 2311c.

When liquid pump diaphragm 2311a contracts, a positive pressure is created in the diaphragm 2111 and once the positive pressure reaches the selected cracking pressure, the diaphragm 2311a flexes away from the cylindrical wall 2351a and flows into mixing chamber 2372. When air pump diaphragm 2311b, 2311c contract, a positive pressure is created and once the positive pressure reaches the selected cracking pressure, diaphragms 2311b, 2311c flex away from the cylindrical wall 2351b, 2351c respectively and air flows into mixing chamber 2372. The air and liquid mix together to form a foamy mixture which is forced out of outlet 2350. The foam mixture may be dispensed as is or may be further refined with the use of foam cartridges, sponges, screens, baffles, or the like and combinations thereof (not shown).

In some embodiments, the liquid pump diaphragm 2311a includes a sponge (not shown) to limit the amount of liquid that may is drawn in and expanded to create different air to liquid mix ratios. In some embodiments, a flow control valve (not shown) is attached to liquid inlet 2352 so that the flow of liquid can be controlled to adjust the air to liquid ratio.

The pump diaphragms 2311a, 2311b, 2311c are expanded and compressed by movement of wobble plate 2314. The shaft 2303 of motor 2304 connects to eccentric wobble plate drive 2326. Wobble plate pin 2327 connects to eccentric wobble plate drive 2326 in an area that is offset from the centerline of the motor shaft 2303. Having the wobble plate pin 2327 offset from the motor shaft 2303 causes circular movement of the wobble plate pin 2327, which causes the ends of the wobble plate 2314 to sequentially undulate. The undulation causes the pump diaphragms 2311a, 2311b, 2311c to sequentially compress and expand to pump the liquid and the air.

Figure 24:
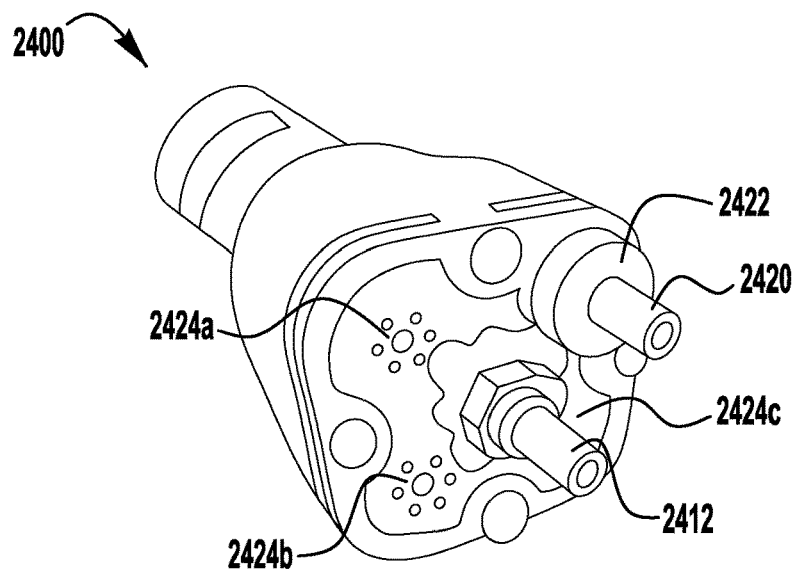
FIG. 24 is a prospective view of an exemplary embodiment of a sequentially operated four diaphragm foam pump.
Figure 25:
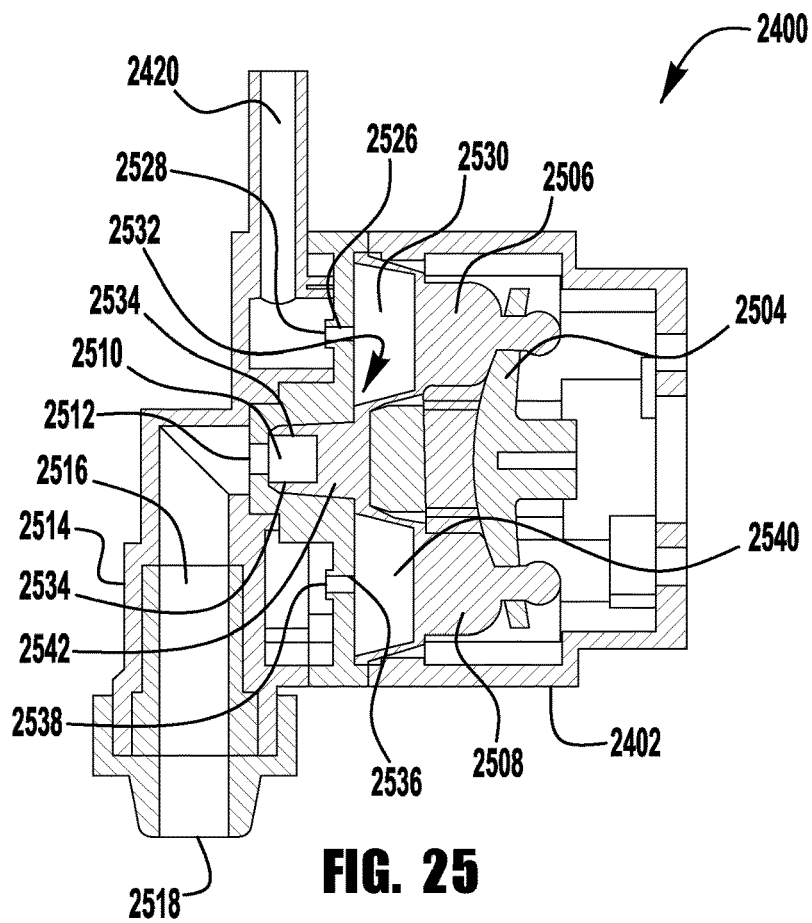
FIG. 25 is a cross-section of an exemplary embodiment of a sequentially operated four diaphragm foam pump.

FIGS. 24 and 25 illustrate another exemplary embodiment of a sequentially-activated multi-diaphragm foam pump 2400. Foam pump 2400 includes a pump housing 2402, liquid inlet valve 2528, three air inlet valves 2538 (only one is shown), a wobble plate 2504, a liquid pump diaphragm 2506, three air pump diaphragms 2508 (only one is shown), mixing chamber 2510, and foam pump outlet 2412. The foam pump 2400 is coupled to, and in fluid communication with, foam cartridge housing 2514, which houses foam cartridge 2516. Foam cartridge 2516 is in fluid communication with outlet nozzle 2518. Foam pump 2400 also includes liquid inlet 2420 that is in fluid communication with a container (not shown) holding foamable liquid. The liquid inlet 2420 is coupled to foam pump 2400 so that the foamable liquid is directed into liquid pump diaphragm 2506.

FIG. 24 is a prospective view of foam pump 2400 and illustrates liquid inlet housing 2422 that is upstream of the liquid pump diaphragm 2506 and three air inlet areas 2424A, 2424B, and 2424C that upstream of and correspond to the three air pump diaphragms 2508. In some embodiments of the pumps described herein, the plurality of pump chambers, e.g. a liquid pump chamber and two or more air pump chambers, are formed by a molded multi-chamber diaphragm.

The liquid pumping portion includes pump diaphragm 2506, liquid pump diaphragm inlet 2526, liquid inlet valve 2528, liquid pump diaphragm chamber 2530, liquid pump diaphragm outlet 2532, and outlet valve 2534. In this embodiment, outlet valve 2534 is integrally molded with the liquid pump diaphragm 2506 and the air pump diaphragms 2508. The liquid pump diaphragm 2506, the liquid pump diaphragm inlet 2526, liquid inlet valve 2528, liquid pump diaphragm chamber 2530, liquid pump diaphragm outlet 2532, and liquid outlet valve 2534 may take any form described herein. Each air pumping portion includes air pump diaphragm 2508, air pump diaphragm inlet 2536, air inlet valve 2538, air pump diaphragm chamber 2540, air pump diaphragm outlet 2542, and outlet valve 2534. Outlet valve 2534 is a cylindrical member that deflects away from the sealing wall when the pump diaphragm is under positive pressure to let the air or liquid flow into the mixing chamber. The air pump diaphragms 2508, air pump diaphragm inlets 2536, air inlet valves 2538, air pump diaphragm chamber 2540, air pump diaphragm outlet 2534, outlet valve 2544 may take any form described herein.

During operation, the liquid pump diaphragm 2506 expands and contracts to pump liquid, and the three air pump diaphragms 2508 expand and contract to pump air. The expansion of the liquid pump diaphragm 2506 opens liquid inlet valve 2528 and draws liquid into the liquid pump diaphragm chamber 2530 through liquid inlet 2526. The expansion of each of the air pump diaphragms 2508 opens the corresponding air inlet valves 2538 and draws air into the corresponding air pump diaphragm chambers 2540. The air enters each air pump diaphragm 2508 through the corresponding air inlets 2536 (only one is shown). Wobble plate 2504 is connected to a motor (not shown), which may take any form described herein. The motor causes the ends of the wobble plate 2504 to sequentially undulate. The undulation causes the liquid pump diaphragm 2506 to compress, which causes outlet valve 2534 to be forced open by the liquid, which flows into the mixing chamber 2510. Outlet valve 2534 is made of a flexible material, such as the same material as the pump diaphragms 2506, 2508, and in some cases the pump diaphragms 2506, 2508 and outlet valve 2534 are formed as one piece. The flexible material allows the outlet valve 2534 to remain closed during expansion of the liquid pump diaphragm 2506, as well as when the liquid pump diaphragm 2506 is in a primed stated. However, during compression of the liquid pump diaphragm 2506, the flexible material of the outlet valve 2534 will be forced open to allow liquid to flow into the mixing chamber 2510.

Subsequently, one of the air pump diaphragms 2508 is compressed by the undulating wobble plate 2504, which causes the outlet valve 2534 to open and air to flow the mixing chamber 2510. The flexible material allows the outlet valve 2534 to remain closed during expansion of the corresponding air pump diaphragms 2508, as well as when the air pump diaphragms 2508 are in a primed stated. However, as with the liquid, during compression of an air pump diaphragm 2508, the flexible material of the outlet valve 2534 will be forced open to allow air to enter mixing chamber 2510. Similarly, the remaining air pump diaphragms 2508 will sequentially compress and pump air into the mixing chamber 2510. The air and liquid mix in the mixing chamber 2510 to create a foam mixture. The foam mixture exits the foam pump 2400 through pump outlet 2412.

As can be seen, the liquid is pumped directly into the mixing chamber 2510 from liquid pump diaphragm 2506. In other words, the liquid does not need to travel through an additional conduit or channel after leaving the liquid pump diaphragm 2506 and before entering the mixing chamber 2510. In some embodiments, the shorter distance between the liquid pump diaphragm outlet 2532 and the mixing chamber 2510 improves the efficiency of the foam pump 2400.

After the foam mixture exits the foam pump 2400, the foam mixture travels through conduit 2546 of foam cartridge housing 2514 and enters foam cartridge 2516. The foam cartridge housing 2514 is an elbow component that directs the foam mixture to flow downward. The downward flow of the foam mixture improves the output efficiency of the foam mixture. However, the foam cartridge housing may take any form that allows the foam mixture to exit through outlet nozzle 2518.

In any of the above-mentioned embodiments, the size of the liquid path as compared to an air path may vary. In certain embodiments, the liquid path is between about 20 times greater and 40 times greater than an air path. Also, in certain embodiments, liquid inlet and/or outlet valves have a higher cracking pressure than air inlet and/or outlet valves.

The exemplary embodiments of foam pumps may be used in a soap or sanitizer dispenser. Refill units as described herein include at least a container for holding a liquid. The refill units are removable from the dispenser and may be replaced with a new refill unit. In some embodiments, the foam pump is a permanent part of the dispenser and the refill unit includes a container and a fitting for connecting to a fitting (not shown) on the foam pump. In some embodiments, the refill unit includes the foam pump that is secured to the containers and the foam pump releasably connects to a drive unit, such as a motor, that is permanently secured to the dispenser. In some embodiments, the refill unit includes the container, the foam pump and motor. In some embodiments, the refill unit includes a power source, such as, for example a battery.

In some embodiments, the dispensers include a direct current (DC) power supply. In some embodiments, the power supply has a voltage of between 3 and 9, including between about 5 and about 9, including between about 6 and about 8, including about 3, including about 4.5, including about 6, including about 7.5, including about 8, and including about 9.

In some embodiments, the dispensers dispense at between about 1 and about 2.5 milliliters/second of foam, including between about 1.9 and 2.5 milliliters/second of foam, including about 1.9 milliliters/second of foam, including about 2.0 milliliters/second of foam, including about 2.1 milliliters/second of foam, including about 2.2 milliliters/second of foam, including about 2.3 milliliters/second of foam, including about 2.4 milliliters/second of foam and including about 2.5 milliliters/second of foam.

A conventional mechanical piston foam pump required 1.8 joules per 12 ml of foam dispensed resulting in 0.15 joules/milliliter of foam. The volume of liquid was 0.9 and the air to liquid ration was 11 to 1. An exemplary pump constructed in accordance with an embodiment the present invention required only 0.6 joules per 12 ml of foam dispensed resulting in 0.05 joules/milliliter of foam. The volume of liquid was 0.5 and the air to liquid ration was 24 to 1.

In some exemplary embodiments, the motor used to drive the foam pump consumes between about 0.4 and about 1.5 joules/12 milliliters of foam output, including between about 0.6 and 1.5 joules/12 milliliters of foam output, including between about 0.5 and 1.3 joules/12 milliliters of foam output, including between about 0.0 and 1.3 joules/12 milliliters of foam output, including between about 0.9 and 1.3 joules/12 milliliters of foam output, including about 0.5 joules/12 milliliters of foam output, including about 0.6 joules/12 milliliters of foam output, including about 0.7 joules/12 milliliters of foam output, including about 0.8 joules/12 milliliters of foam output, including about 0.9 joules/12 milliliters of foam output, including about 1.0 joules/12 milliliters of foam output, including about 01.1 joules/12 milliliters of foam output, including about 1.2 joules/12 milliliters of foam output, including about 1.3 joules/12 milliliters of foam output.

In some embodiments the volume of foam output is between about 60-130 milliliters of foam, including between about 100-120 milliliters of foam, including about 80 milliliters of foam, including about 90 milliliters of foam, including about 100 milliliters of foam, including about 110 milliliters of foam and including about 120 milliliters of foam.

In some embodiments the volume of foam output has a foam density of between about 0.08 and about 0.125 grams per milliliter of foam, including a foam density of about 0.08 grams per milliliter of foam, including a foam density of about 0.09 grams per milliliter of foam, including a foam density of about 0.1 grams per milliliter of foam, including a foam density of about 0.11 grams per milliliter of foam and including a foam density of about 0.12 grams per milliliter of foam.

In some embodiments, the foam pump is configured to produce a foam that has an air ratio of about 10 to 1. In some embodiments, the foam pump is configured to produce a foam that has an air ratio of about 9 to 1. In some embodiments, the foam pump is configured to produce a foam that has an air ratio of about 8 to 1. In some embodiments, the foam pump is configured to produce a foam that has an air ratio of about 7 to 1. In some embodiments, the foam pump is configured to produce a foam that has an air ratio of about 6 to 1.

Although the embodiments described above generally included pumps that have one liquid pump chamber and multiple air chambers, in some embodiments the pumps have more than one liquid pump chamber. In some embodiments, the pumps have two or more liquid pump chambers. In some embodiments, the two or more liquid pump chambers pump two or more different liquids.

Figure 26:
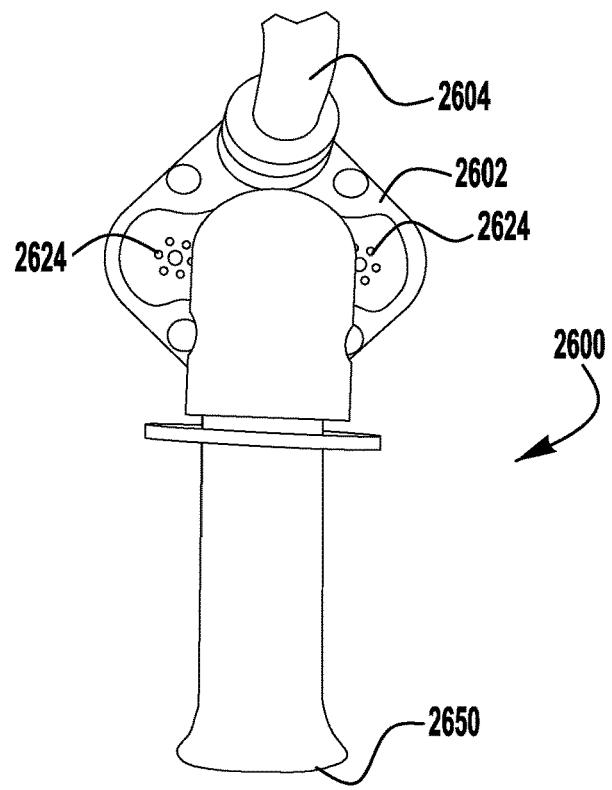
FIG. 26 is a prospective view of an exemplary outlet nozzle.

FIG. 26 is a prospective view of an exemplary foam outlet nozzle 2600 that provides ultra high volume foam soap. In this exemplary embodiment, outlet nozzle 2600 is connected to a four chamber sequentially activated diaphragm foam pump 2602 described herein, however, the outlet nozzle 2600 may be used with other pumps. Pump 2602 includes a liquid inlet 2604 and three air inlets 2624 (only two are visible) and an outwardly flared outlet nozzle 2650.

Figure 27:
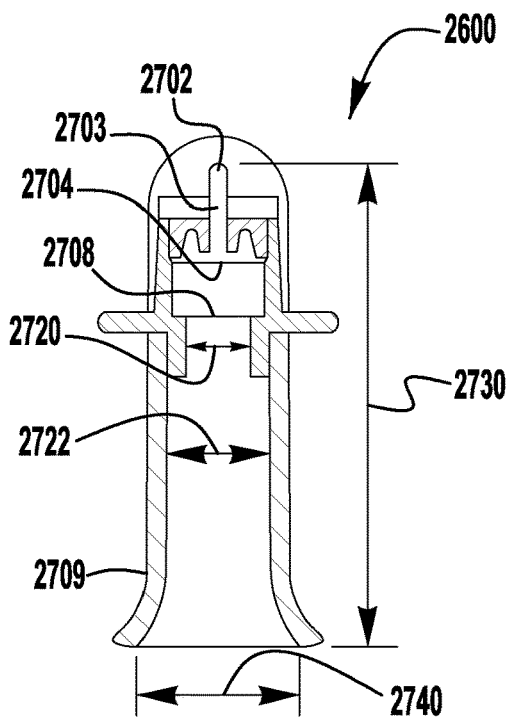
FIG. 27 is a cross-sectional view of the exemplary outlet nozzle of FIG. 26.

FIG. 27 is a cross-sectional view of the exemplary foam outlet nozzle 2600 of FIG. 26. Foam outlet nozzle 2600 includes a fluid inlet 2702. Fluid inlet 202 receives a liquid/air mixture from foam pump 2602. The fluid travels through passage and passes through mix media 2704, which may be, for example a screen which causes turbulence in the mixture to create foam. The foamy mixture passes through a second mix media 2708, which may also be, for example, a screen. Although this exemplary embodiment contains two mix media 2704, 2708, it has been discovered that only one mix media 2708 provides a high quality foam in the novel design of the outlet nozzle 2600. The foamy mixture passes through a passage having an inside diameter 2720 and into a second passage having an inside diameter 2722. In some embodiments, the inside diameter 2720 and 2722 have an inside diameter of between about 0.2 inches and about 0.35 inches. Foam outlet nozzle 2600 includes a flared tip 2710. In some embodiments, flared tip 2710 has an inside diameter of between about 0.5 inches and about 0.7 inches. In addition, it has been discovered that the length 2730 of the spout 2709 has an effect on the quality of the foam output through the foam outlet nozzle 2600. In some embodiments, the length 2730 of the spout is between about 0.3 inches and about 1.25 inches. Exemplary embodiments of foam outlet spout 2600 have produced foam densities as low as 0.04 grams/cubic cm, as low as 0.04 grams/cubic cm, as low as 0.03 grams/cubic cm and as low as 0.02 gram/cubic cm. Without limiting effect, it is believed that high foam volume is due to the large diameter spout 2709 and the flared tip 2710. The hold leading into the tube cannot be too small or foam will breakdown.

In some exemplary embodiments the liquid cylinder (not shown) of the foam pump 2602 utilize a mechanism to throttle the liquid flow entering foam pump 2602, such as, for example, lost motion, smaller diameter liquid diaphragm, a restrictor valve, a restrictor inlet, a sponge located within the liquid diaphragm, or the like. In some embodiments, depending on the soap formulation level of alcohol and surfactant type the nozzle 2600 of the foam pump 2602 may differ in design. A larger diameter nozzle with a single screen will foam a soap formulation that is harder to foam, such as a soap with alcohol or a non-ideal surfactant and create a foam with large bubbles. A better foaming formulation will be able to create a high volume foam with consistent and small bubbles when mated with a smaller nozzle diameter and dual screens.

While the present invention has been illustrated by the description of embodiments thereof and while the embodiments have been described in considerable detail, it is not the intention of the applicants to restrict or in any way limit the scope of the appended claims to such detail. Additional advantages and modifications will readily appear to those skilled in the art. Moreover, elements described with one embodiment may be readily adapted for use with other embodiments. Therefore, the invention, in its broader aspects, is not limited to the specific details, the representative apparatus and illustrative examples shown and described. Accordingly, departures may be made from such details without departing from the spirit or scope of the applicants' general inventive concept.

The invention claimed is:

1. A foam dispenser comprising:
   a housing;
   a drive motor;
   a foam pump operatively coupled to the drive motor;
   the foam pump is secured to the housing and the foam pump includes:
      a housing;
      a molded multi-chamber diaphragm;
         the molded multi-chamber diaphragm comprising:
            a liquid pump chamber;
            two or more air pump chambers; and
            one or more outlet valves;
         a mixing chamber downstream of the one or more outlet valves for mixing foamable liquid from the liquid pump chamber with air from each of the two or more air pump chambers;
      a foam cartridge in fluid communication with the mixing chamber; and
      an outlet for dispensing foam wherein the outlet is in fluid communication with the foam cartridge.

2. The dispenser of claim 1 wherein the molded multi-chamber diaphragm further comprises a fluid inlet valve and two or more air inlet valves.

3. The dispenser of claim 1 further comprising a quick-disconnect connector in fluid communication with the foam pump for connecting to a connector on a refill unit.

4. The dispenser of claim 1 further comprising a refill unit.

5. The dispenser of claim 1 wherein the molded multi-chamber diaphragm comprises at least three air pump chambers.

6. The dispenser of claim 1 further comprising a flow control valve for controlling the flow of liquid to the liquid pump chamber.

7. The dispenser of claim 1 wherein the liquid pump chamber pumps a liquid volume of between about 0.1 and about 1.0 ml of liquid for each dose of foam dispensed.

8. The dispenser of claim 1 wherein the liquid pump chamber is compressed between 5 and 15 times for each dispense of foam.

9. The dispenser of claim 1 wherein the foam pump is configured to produce a foam that has an air to liquid ratio of about 6 to 1 to about 8 to 1.

10. The dispenser of claim 1 further comprising a direct current power supply, wherein the power supply has a voltage of between about 3 and 8.

11. The dispenser of claim 1 further comprising a direct current power supply, wherein the power supply has a voltage of about 6.

12. The dispenser of claim 1 wherein the motor consumes between about 0.05 to about 0.125 joules per milliliter dispensed.

13. The dispenser of claim 1 wherein the dispenser dispenses foam at a rate of about 2.0 to 2.4 milliliters per second.

14. A refill unit for a foam dispenser comprising:
a container for holding foamable liquid;
a foam pump secured to the container wherein the foam pump includes:
a housing;
a molded multi-chamber diaphragm;
the molded multi-chamber diaphragm comprising:
a liquid pump chamber; and
three air pump chambers;
an inlet valve; and
an outlet valve
a mixing chamber downstream of the outlet valve for mixing foamable liquid from the liquid pump chamber with air from each of the three air pump chambers;
a foam cartridge in fluid communication with the mixing chamber; and
an outlet for dispensing foam wherein the outlet is in fluid communication with the foam cartridge.

15. The refill unit of claim 14 further comprising a plate connected to the liquid pump diaphragm and the air pump diaphragm;
wherein movement of the plate causes at least a partial dose of liquid to be pumped into the mixing chamber, followed by at least a partial dose of a first dose of air being pumped into the mixing chamber, followed by at least a partial dose of a second dose of air being pumped into the mixing chamber, followed by at least a partial dose of a third dose of air being pumped into the mixing chamber.

16. A foam dispenser comprising:
a dispenser housing;
a foam pump secured to the housing wherein the foam pump includes:
a pump housing;
a molded multi-chamber diaphragm;
the molded multi-chamber diaphragm comprising:
a liquid pump chamber; and
two or more air pump chambers;
a rotatable drive mechanism for sequentially compressing the liquid pump chamber and two or more air pump chambers;
the rotatable drive mechanism coupled to a drive motor;
a mixing chamber downstream of the liquid and air pump chambers for mixing foamable liquid from the liquid pump chamber with air from each of the three air pump chambers;
a foam cartridge in fluid communication with the mixing chamber; and
an outlet for dispensing foam wherein the outlet is in fluid communication with the foam cartridge.

17. The foam dispenser of claim 16 wherein the foam pump is configured to produce a foam density of between about 0.08 and between about 0.125 grams/liter.

18. The dispenser of claim 16 wherein the foam pump is configured to produce a foam that has an air to liquid ratio of about 6 to 1 to about 8 to 1.

19. The dispenser of claim 16 further comprising a direct current power supply, wherein the power supply has a voltage of between about 3 and 8.

20. The dispenser of claim 16 further comprising a motor, wherein the motor consumes between about 0.6 to about 1.5 joules per milliliter dispensed.

* * * * *